United States Patent [19]

Judy et al.

[11] Patent Number: 4,878,891

[45] Date of Patent: Nov. 7, 1989

[54] METHOD FOR ERADICATING INFECTIOUS BIOLOGICAL CONTAMINANTS IN BODY TISSUES

[75] Inventors: Millard M. Judy; James L. Matthews; Joseph T. Newman; Franklin Sogandares-Bernal, all of Dallas, Tex.

[73] Assignee: Baylor Research Foundation, Dallas, Tex.

[21] Appl. No.: 67,237

[22] Filed: Jun. 25, 1987

[51] Int. Cl.$^4$ .............................................. A61K 39/00
[52] U.S. Cl. ........................................ 604/5; 424/101
[58] Field of Search .............. 128/1 R, 395; 604/4–6; 424/101

[56] References Cited

U.S. PATENT DOCUMENTS

| | | | |
|---|---|---|---|
| 4,613,322 | 9/1986 | Edelson | 128/1 R |
| 4,684,521 | 8/1987 | Edelson | 424/101 |
| 4,708,715 | 11/1987 | Troutner et al. | 604/6 |
| 4,727,027 | 2/1988 | Wiesehahn et al. | |

OTHER PUBLICATIONS

Webster's New International Dictionary of the English Language, Second Edition, 1935, pp. 2416–2417, under "spectrum".

Doiron's article, "Photophysics of and Instrumentation for Porphyrin Detection and Activation", *Porphyrin Localization and Treatment of Tumors*, Proceedings of the Clayton Foundation International Symposium on Porphyrin Localization and Treatment of Tumors, Santa Barbara, Calif., Apr. 24–28, 1983, Alan R. Liss, Inc., New York, N.Y., 1984, pp. 41–73.

*Primary Examiner*—C. Fred Rosenbaum
*Attorney, Agent, or Firm*—Johnson & Gibbs

[57] ABSTRACT

A method for externally eradicating infectious pathogenic contaminants, such as enveloped viruses, bacteria, trypanosomal and malarial parasites, present in body tissues, such as blood, blood components, semen, skin, and cornea, before the treated body tisues are introduced into, or transplanted onto, the body of a human or an animal. Such method includes the steps of: (1) admixing an effective, non-toxic amount of photoactive compound, whch has a selectivity for binding to the infectious pathogenic biological contaminants present therein, with the body tissues outside the body to produce a resulting body tissues; (2) passing the resulting body tissues through an irradiating cell assembly, and (3) irradiating the resulting body tissues in the irradiating path of the cell assembly for an effective period of time with an effective level of radiation such that the radiation penetrates the resulting body tissues and eradicates the photoactive-compound-bound contaminants present in the resulting body tissues and produces a decontaminated body tissue suitable for introducing into, or transplanting onto, the body of a human or animal.

63 Claims, 5 Drawing Sheets

REFLECTING MIRROR

REFLECTING MIRROR

METHOD FOR ERADICATING INFECTIOUS BIOLOGICAL CONTAMINANTS IN BODY TISSUES

BACKGROUND OF THE INVENTION

1. Field of the Invention

The present invention relates generally to decontamination of body tissues; and more particularly, but not by way of limitation, to external eradication of infectious pathogenic biological contaminants from blood or blood products prior to intravenous injection of such blood or blood products into a patient's body.

The present invention also relates to external eradication of infectious pathogenic biological contaminants from skin, cornea or semen prior to transplanting or introducing of such tissues into the recipient's body.

2. Brief Description of the Prior Art

Blood and blood products have been employed as therapeutic agents since the 19th century. It was, however, not until the early 1900's that transfusion of stored, anticoagulated blood became a reality when the first blood banks were organized in Chicago and New York City. Almost half a century later, in 1982, an estimated 9,349,700 units of whole blood were collected in the U.S. by 5400 blood banks and transfusion services.

One of the many problems that plagues the use of blood transfusions is the transmission of agents causing infectious disease. A number of these infectious agents are of serious clinical importance in that such agents are not only dangerous to the recipient patients, but can also pose a danger to physicians, and other hospital personnel, handling the blood and blood products.

Many efforts have been made to ensure that the blood to be transfused is free of pathogenic biological contaminants. So far, screening of blood donors and blood samples is the only effective method to ensure that the blood to be transfused is not contaminated with infectious agents. Unfortunately despite screening techniques, infections still occur following blood transfusions.

U.S. Pat. No. 3,041,242 describes a process for eradication of virus contained in dried plasma wherein the dried plasma is heated at an elevated temperature for a length of time followed by applying a gas lethal to microorganisms, under high vacuum conditions. However, the method is not applicable to the treatment of human whole blood; and the viability of the dried plasma would most likely be impaired during the process.

It has been documented that certain cells may be killed by irradiation after treating them with certain photochemicals. Attempts to use light absorbing dyes to trigger photoreactions in biological systems date back to early 1900's. For example, Jesionek and Tappenier in 1903 used white light to activate topically applied eosin on skin tumors. (Jesionek, A. and Tappenier, V.H. Aur Behandlung des Hautcarcinomes mit Flueszierenden Stoffen. Munch. Med Wochenschr. 41:2042-2044, 1930).

It has been known for over 30 years that hematoporphyrin derivatives accumulate in neoplastic, embryonic, and regenerating tissues. Thus, injected hematoporphyrin has been found to have localized and fluoresced in several types of tumor induced in mice (Figge, F.H.J., Weiland G.S., Mangiollo, L.0.: Cancer Detection and Therapy. Affinity of Neoplastic, Embryonic, and Traumatized Tissues for Porphyrins and Metalloporphyrins. Proc. Soc. Exp. Biol. Med. 64: 640-641, 1948)

The red fluorescence of hematoporphyrin has also been observed under ultraviolet light in various malignant tumors in patients who had been given large doses of crude mixtures of hematoporphyrin compounds (hereinafter referred to as Hpd) (Rasmussen-Taxdal, D.S., Ward, G.E., and Figge, F.H.J.: Fluorescence of Human Lymphatic and Cancer Tissues Following High Doses of Intravenous Hematoporphyrin. Cancer 8: 78-81, 1955). As a result, methods have been developed to capitalize on the unique property of Hpd as a tumor marker in the detection and localization of different forms of cancer (King, E.G., et al., Hematoporphyrin Derivative as a Tumor Marker in the Detection and Localization of Pulmonary Malignancy, *In Recent Results in Cancer Research,* Vol. 82, Springer-Verlag, Berlin-Heielberg, 1982, 90; Benson, R.D., et al, Detection and Localization of In Situ Carcinoma of the Bladder with Hematoporphyrin Derivative. Mayo Clinic Proc., 57:548, 1982).

Although the unique photodynamic properties of Hpd, as well as its affinity toward tumor cells, had long been known, it was more than half a century later that the potential of using Hpd to selectively destroy tumor cells was explored. The bulk of the research on the use of Hpd to selectively destroy tumor cells in human has been reviewed by Dougherty et al. (Dougherty, T. J. et al., Photoradiation Therapy-clinical and Drug Advances. *In Porphyrin Photosensitization,* D. Kessel and T.J. Dougherty, Eds., Plenum Press, N.Y., PP. 3-13, 1983).

The emphasis on using Hpd as the photoactivating or light-activating compound in photoradiation of tumors is based on two important properties of Hpd. Firstly, as judged by fluorescence, Hpd is preferentially accumulated, and retained to a higher degree in malignant tumors than in surrounding normal tissue or benign tumors. Secondly, when properly photoactivated, Hpd causes the destruction of cells and tissue in which it resides. The generally accepted mechanism of cell kill by Hpd is that when activated by appropriate light, the Hpd can undergo an energy transfer process with oxygen to form a singlet oxygen, which subsequently oxidizes, hence kills the cells or tissues to which it has attached as a substrate. (Weishaupt,-K.R., Gomer, C.J. and Dougherty, T.J. Identification of Singlet Oxygen as the Cytotoxic Agent in Photoinactivation of a Murine Tumor. Cancer Res. 36: 2326-2329, 1976).

Despite the enormous progress and research in the use of light-activated photosensitizer, such as Hpd, to pinpoint the location of malignant tumor cells and to eradicate them, relatively little work has been done to determine if such a photosensitizer will behave similarly toward virus, bacteria, fungi, protozoa, or other parasites.

U.S. Pat. No. 4,649,151 to Dougherty, et al., discloses the preparation, purification and utilization of tumor-selective, photosensitizing drugs (i.e. mixtures of porphyrins) in the localization and treatment of neoplastic tissue, such as tumors or cancers in patients and animals. A time delay of several hours to several days is required between injection of the drug and illumination in order for the drug to metabolically clear normal tissue and hence achieve the best therapeutic ratio of drug in tumor cells to drug in normal cells. One of the objects set forth in Dougherty, et al., is to provide a drug which is selective to certain pathogens within an animal or within blood, blood plasma or serum or fractions thereof and which permits photochemical destruction of the pathogens in vivo or in vitro. However, the reference contains no teaching or suggestion of the external purification of human tissues such as human blood, blood plasma, serum, semen, skin or cornea utilizing a mixture of porphyrins to eradicate infectious pathogens and to provide purified and sterilized human tissues such as human blood, human blood plasma, human serum, semen, skin or cornea which can be infused or introduced into a patient's body.

The Dougherty, et al., patent also fails to demonstrate the tolerance of either human blood, human blood plasma, or human serum outside the body toward the drug. Moreover, no evidence was provided to demonstrate that either human blood, human blood plasma, human serum, or other human tissues outside the body remains unchanged after the irradiation of such blood, blood plasma, serum, or other tissues containing the described drug. Similarly, neither the effective range of concentrations of the described drug nor the effective range of radiation is disclosed for its use outside an animal or human body.

U.S. Pat. No. 4,614,190 to Stanco, et al., discloses an arrangement for effecting photoirradiation of tumor and cancerous tissues in human or animal body. The patent discloses the method of pulsing the electromagnetic energy to activate, in situ, administered hematoporphrin derivative contained within the tissue in the body so that the surrounding flesh is not unduly affected.

This reference, however, neither teaches nor suggests the external purification of tissues such as blood, blood plasma, serum, semen, skin or cornea utilizing a mixture of porphyrins to eradicate infectious pathogens and to provide purified and sterilized tissues such as blood, blood plasma, serum, semen, skin or cornea which can be infused or introduced into the recipient's body.

The Stanco, et al., patent also fails to demonstrate the tolerance of either blood, blood plasma, serum, or other tissues outside the body toward the drug. Furthermore, no evidence was provided to demonstrate that either blood, blood plasma, serum, or other tissues outside the body remains undamaged after the irradiation of such blood, blood plasma, or serum, or other tissues containing the described drug. Similarly, neither the effective range of concentrations of the described drug nor the effective range of radiation is disclosed for its use outside an animal or human body.

Studies using fluorescence and laser techniques have suggested that hematoporphrin derivative (Hpd) would bind to parasites *Plasmodium berqhei, P. vivax* and *P. falciparum*. Moreover, whole animal studies utilizing a mixture of HPD and Chloroquine, an antimalarial drug, have reflected the reduction of the parasitemia in mice infected with Chloroquine resistant *P. berghei.* (F. Sogandares-Bernal, J.L. Matthews and M.M. Judy, HPD—Induced Reversal of Chloroquine Resistance to Malaria, a lecture presented at International Symposium on Malaria, held on June 1-5, 1986, at Instituo Oswaldo Cruz, Rio de Janeiro, Brazil,also in press, Mem. Inst. Oswald Cruz).

A few investigators have reported photoinactivating bacterial viruses and animal viruses using heterocyclic dyes (Yamamoto, N., Nitrogen Fixation by A Facultatibe Bacillus, J. Bacteriology, 75: 403, 1958; Hiatt, C.W., et al: Inactivation of Viruses by the Photodynamic Action of Toluidine Blue, J. Immunology, 84: 480–84, 1960). The plaque formation capability of *Herpes simplex* virus has also been reported to be hampered by the treatment of virus in culture with a combination of a hematoporphrin derivative and visible light. (Lewin, A.A., et al, Photodynamic Inactivation of Herpes simplex Virus by Hematoporphyrin Derivative and Light, Proc. Soc. Exp. Biol. Med. 163: 81–90, 1980).

Similarly, it has been reported that, in culture, the plaque formation by *Herpes simplex* virus type 1, Cytomeqalo-virus, or measles virus is reduced, by more than 99%, by the combination effect of Hpd and Rhodamine B dyelaser light, with an energy density of 20 J/cm$^2$. On the other hand, the echovirus type 21, which lacks an envelope, is not affected under similar conditions (H. Skiles, M.M. Judy, and J.P. Newman, Photodynamic Inactivation of Viruses With Hematoporphyrin Derivatives, Abstract A 38, American Society for Microbiology page 7, 1985). The combined effect of light and Photofrin II TM on *Herpes simolex* virus type 1 grown in culture can be observed in a flow cell system made up of loops of transparent tubing attached to a glass slide, with a 1000W Xeon light equipped with a red filter serving as the light source. (F. Sogandares-Bernal, J. L. Matthews, H. Skiles, M.M. Judy, and J. Newman, Photoactivation of *Herpes simplex* virus by Photofrin II and Light in A Flow Cell System, 1987 ASM Annual Meeting, Atlanta, Ga., 1–6 March 1987).

Extracorporeal treatments of certain noninfectious cancers have been known for more than a decade. (H. Hyden, L.E. Gelin, S. Larsson, and A. Saarne, A New Specific Chemotherapy: A Pilot Study With An Extracorporeal Chamber. Rev. of Surgery (Philadelphia), 31: 305–320, 1974; H. Wolf, E. Langvad, and H. Hyden, The Clinical Course In Patients With Renal Carcinoma Subjected To Extracorporeal Immunoadsorption, British J. Urology, 53: 89–94, 1981). Recently, it was reported that the activity of a noninfectious cancer but nevertheless potentially deadly, cutaneous T-cell lymphoma, could be controlled by extra corporeal photochemotherapy. In the therapy, after patients were orally given 8-methoxypsoralen, blood was removed from the patient and the lymphocyte-enriched blood fraction was exposed to ultraviolet A. Subsequently, the damaged lymphocyte-enriched blood fraction was returned to the body of the patient. An immune reaction to the infused damage cells then restricted the activity of the abnormal cancer cells in the patient's body. (R. Edelson, et al., Treatment of Cutaneous T-Cell Lymphoma by Extracorporeal Photochemotherapy, New England J. Medicine, 316: 297–303, 1987).

The purpose of the extracorporeal photochemotherapy as reported by Edelson, et al., was not to damage as many cells as possible outside the patient's body. Rather, only a small fraction of the cells was damaged which was then reintroduced into the patient's body to serve as a "vaccine" for triggering an immune reaction in the body.

Despite the progress in photochemotherapy, no work, however, has been reported concerning the utility of such method to eradicate viruses present either in human whole blood or in other body tissues outside the body. Similarly, no one has reported the use of photoinactivation in a clinical setting to remove infectious agents, such as viruses, bacteria, fungi and protozoa, from human whole blood used for transfusion.

Viruses are, of course, completely different from malignant tumor cells. Unlike malignant tumor cells which are "uncontrollable" cells in human body, viruses are extremely tiny invaders. Tumor cells are visible under an ordinary microscope; in contrast, viruses are visible only with the aid of a high power electron microscope. Moreover, viruses lack most of the genetic materials present in malignant tumor cells. Indeed, a virus mainly consists of a very small number of genes, made up of either ribonuceleic acid (RNA) or deoxyribonucleic acid (DNA), encased, perhaps, in a protective coating of protein. Furthermore, diseases caused by viruses are contagious. In contrast, cancers composed of malignant tumor cells are not known to be contagious.

In view of the total difference between tumor cells and viruses, it is not surprising that clinically useful anticancer drugs are mostly ineffective for the treatment of viral diseases, and vice versa. Thus, as expected, 3-deoxy-3'-azidothymidine (AZT), currently one of the few experimental drugs used to control the proliferation of virus that causes the acquired immune deficiency syndrome (AIDS) is totally ineffective in preventing the proliferation of tumor cells. Likewise, Vincristine, a powerful anticancer drug, is ineffective in the treatment of viral diseases.

The word virus comes from the Latin for slimy liquid, stench, poison. The connotation is appropriate in view of the fact that untold number of varieties of viruses have long preyed on humans, animals and plants. Indeed, these infinitesimal, bizarre creatures may be mankind's deadliest enemy.

For examples, Hepatitis-B virus causes a hepatitis infection which may develop into cirrhosis in which the liver becomes a mass of fiber-like tissue. In hepatitis, liver function is impaired and, in some cases, the condition can be fatal. There are approximately 200,000 cases of reported hepatitis infections per year in this country. In addition, there may be as many as a few million carriers of hepatitis.

The human immunodeficiency virus (HIV), a retrovirus, is the cause of acquired immune deficiency syndrome (AIDS) which is invariably fatal. So far, the AIDS virus has infected more than a million people in this country alone. About one-third to one-half of the infected individuals will develop the disease. Worst yet, because the AIDS virus has a long and undeterminate period of incubation, a person can unknowingly carry and spread the deadly disease for years. The invariably fatal viral disease AIDS can be transmitted by the exchange of body tissues or body fluids such as blood, blood products, or semen. Indeed, hemophiliacs and others receiving blood transfusions account for about 3% of the reported AIDS cases in this country between 1981 and late 1986. Artificial insemenation, organ transplant, and transplant of skin, cornea and other tissues can also transmit this fatal viral disease.

In the presence of some co-factors, human T-cell leukemia virus, another retrovirus, can cause leukemia in human beings.

Smallpox, prior to its eradication, caused epidemics that devasted human populations in the 18th century. Polio virus is the cause of Poliomyelitis which infected some 400,000 Americans during its peak from 1943 to 1956, killing about half of them by paralysis and respiratory failure. Cytomegalovirus accounts for approximately half of all interstitial pneumonitis that occur in bone marrow transplant patients. It is a major cause of pneumonia in immunosuppressed patients, who often die from such illness. Furthermore, estimates vary, but from 20-30% of all persons in the U.S. receiving blood as a result of surgical procedures develop a post-transfusion syndrome believed to be caused blood infected with Cytomegalovirus.

*Herpes simplex* virus is the cause of oral, ocular, and genital sores for which there is no cure. Mumps virus is the cause of mumps, a disease which sometimes leads to aspermia due to complications.

Influenza virus that mutates every few years is the cause of Influenza for which there is no cure. Although most victims of influenza virus recover after a few days of suffering, the disease can sometimes be fatal.

Another harmful virus is adenovirus which is the cause of respiratory infections, such as sore throat. Rhinovirus is the cause of the common cold for which there is also no cure. There are approximately 200,000 cases of varicella (chicken pox) in the U.S.; whereas, zoster (shingles), a recurrent form of the disease affects about 2% of the population. Both of these diseases are caused by the same virus. The Epstein-Barr virus has been associated with infectious mononucleosis and hepatitis. The rate of infection with Epstein-Barr virus is approximately 150 cases per 100,000 population.

Viruses cause such a significant number of diseases in the population that these microorganisms sometimes threaten to reduce the number of people available to carry out the functions of the society. These viruses often attack the productive people in which society has made an investment.

People infected with virus may carry these agents or their particles in their blood. Likewise, people attacked by infectious diseases often carry pathogenic microorganisms or other contaminants in their blood. Consequently, blood donated or sold to blood banks may be contaminated with virus or other biological and pathogenic contaminants.

Most blood samples are now being tested for the presence of certain virus. These tests usually involve the determination of the presence of antibodies to various viruses or the viral antigen itself, such as HBsAg. Although most of the tests employed to test blood samples are generally quite accurate, they are not infallible. Also, due to cost considerations, not all blood is tested for the presence of pathogenic contaminants, including viruses. Most importantly, because antibodies do not form immediately after exposure to the virus, a newly infected person may unknowingly donate blood after becoming infected but before the antibody has a chance to manifest a positive test. It has also been documented that some people infected with certain viruses simply do not produce detectable antibodies against them.

A large number of diseases, some of which are either fatal or of serious clinical importance, can be transmitted by transfusion. Since pathogenic organisms are found in different fractions of whole blood, risks of post-transfusion diseases vary depending on the blood product or component used. In general, the risk for any disease is directly proportional to the volume of blood transfused and to the numbers of infectious organisms contained therein.

For example, post-transfusion hepatitis has long been a serious medical problem. In 1970, the National Research Council estimated that there were approximately 30,000 cases of clinical post-transfusion hepatitis per year with a mortality rate of about 10 percent. It was also estimated that there may be up to five times that many cases that are not clinically detectable. Other studies estimate the risk at about 7 cases per 1,000 units of blood transfused, with one-third of these being icteric. More recent studies, however, suggest a higher risk. The risk has been estimated as between 7 and 10 percent of all blood recipients. The risk of post-transfusion hepatitis is increased when blood from commercial donors is used. The introduction of universal hepatis B surface antigen (HBsAg) testing on all blood donated in this country has resulted in a reduction of type B related post-transfusion hepatitis. However, there continues to occur cases of type B post-transfusion hepatitis caused by blood showing negative HBsAg, hepatitis B surface antigen, as determined by the most sensitive tests currently available. Moreover, there is no reliable test for the detection of other forms of hepatitis, including hepatitis A, and non-A non-B. As discussed above, hepatitis infection not only is sometimes fatal by itself, the disease also may lead to fatal cancer of the liver, or may lead to additional complications in a patient already weakened by surgical or other trauma.

Another infectious disease most commonly transmitted by blood transfusion is caused by Cytomegalovirus which can precipitate the fatal interstitial pneumonitis. It has been shown that about 35 percent of patients who have been infused with fresh whole blood become infected with Cytomegalovirus.

Yet another infectious disease transmitted by blood transfusion is malaria. The incidence of transfusion-induced malaria has recently increased at an alarming rate. More than a million human beings infected with drug-resistant malaria are believed to die each year in Africa alone. There were more than 485,000 drug-resistant cases of malaria documented in Brazil during the first six months of 1986. In fact, many of the malaria infections in the world are now caused by parasites resistant to the most effective and least dangerous antimalarial agent, chloroquine. In erythrocytic phase, the malarial parasites reside exclusively in erythrocytes and are transmitted only with transfusion of products containing red blood cells. Without treatment, malaria can be fatal. These drug-resistant cases of malaria have proven most difficult to treat.

Still another hazard of blood transfusion is syphilis; although it does occur, the incidence is not very high. Nevertheless, syphilis is not a disease to be treated lightly. The disease can cause havoc to babies born of disease-carrying mothers. The disease can also cause cardiovascular and neurological complications. Chagas' disease, African trypanosomiasis, kala-azar, toxoplasmosis, and infections with microfilaria are other infectious agents that may be transmitted by transfusion of whole blood.

It is clear that despite screening techniques, infections with viruses and other biological pathogenic contaminants still occur following blood transfusions. In the setting of clinical medicine, the processing and handling of body fluids, such as blood, imposes a threat of a number of possible infections to physicians and other hospital workers, and patients. Currently, there is no effective procedure for decontaminating the infected body fluid, such as human whole blood or its formed elements.

It is, therefore, highly desirable to have a safe and economical method and apparatus that will eradicate pathogenic viruses, microorganisms, or parasites present in human whole blood or blood products before such products are infused into a recipient, hence, infecting the recipient with such disease producing agents. At the same time properly decontaminated blood will also spare the daily threat of infections to hospital personnel who must handle these body fluids. This need is even more acute in a blood bank where donor blood and blood products are stored and processed.

It is equally desirable to have a safe and economical method and apparatus that will eradicate pathogenic viruses, microorganisms, or parasites present in human or animal tissues, such as skin, cornea, and semen, before such tissues are introduced or transplanted into a recipient, hence, infecting the recipient with such diseases.

Since there is so far no cure for AIDS, it is also desirable to have a safe method and apparatus to reduce the viremia in AIDS patients to prolong the lives of such patients.

It is toward such goals that the present invention is directed.

SUMMARY OF THE INVENTION

According to the present invention an efficient and economical method for treating body tissues to eradicate infectious pathogenic biological contaminants, such as envelope-containing viruses, bacteria, malarial, trypanosomes, and other parasites, which may be present in said body tissues is provided wherein the contaminants are eradicated prior to introduction of the treated body tissues into the body of a patient. Broadly, the method comprises:

(a) introducing or admixing an effective, non-toxic amount of a photoactive compound with the body tissue to produce a resulting body tissue, the photoactive compound having a selectivity for binding to the infectious pathogenic biological contaminants present in the body tissue;

(b) passing the resulting body tissue through a cell assembly having a predefined flow path or suspending the resulting body tissue in a solution, and (c) irradiating the resulting body tissue in the path of the cell assembly for an effective period of time with an effective level of radiation such that the radiation penetrates the resulting body tissue and eradicates the photoactive-compound-bound contaminants and produces a decontaminated body tissue suitable for introduction into the body of a patient.

An object of the present invention is to provide an improved method for externally eradicating infectious pathogenic biological contaminants from blood and blood products.

Another object of the present invention is to provide an efficient and economical method to externally eradicate infectious pathogenic biological contaminants from blood and blood products so that the blood and blood products are safe for introduction into the body of a patient.

Still another object of the present invention is to provide an efficient and economical method for externally eradicating infectious pathogenic biological contaminants from blood or blood products so that the blood or blood products are safe for handling.

Another object of the present invention is to provide an effective and economical method for external eradication of pathogenic enveloped viruses, other microorganisms, or other pathogenic biological contaminants in tissues intended for transplantation to humans.

Yet another object of the present invention is to provide an effective and economical method for external eradication of pathogenic enveloped viruses, other microorganisms, and parasites, or other pathogenic biological contaminants in protein and other materials intended for intravenous administration to humans or animals.

Other objects, advantages and features of the present invention will become clear from the following detailed description when read in conjunction with the drawings and appended claims.

BRIEF DESCRIPTION OF THE DRAWINGS

FIG. 3-a is a diagram showing a three-dimensional rectangular coordinate system for the irradiation cell of FIG. 3.

FIG. 4-a is a diagram showing a three-dimentional rectangular coordinate system for the irradiation cell in FIG. 4.

FIG. 5-a is a diagram showing a three-dimentional rectangular coordinate system for the irradiation cell in FIG. 5.

DESCRIPTION OF THE PREFERRED EMBODIMENT

Figure 1:
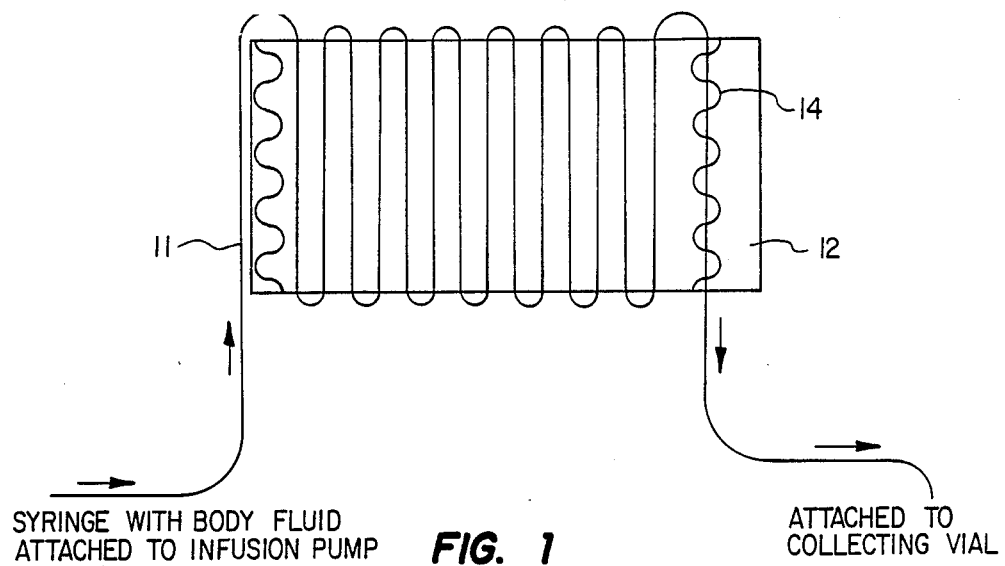
FIG. 1 is a schematic representation of a cell assembly having a predetermined flow path in the form of a flexible transparent tubing wherein fluids passing along the flow path are exposed to radiation.

The present invention provides a method for externally eradicating infectious pathogenic contaminants, such as enveloped viruses, microorganisms, parasites, bacteria and the like, from body tissues that the likelihood of a person becoming infected as a result of receiving a transfusion or transplantation of the body tissue is substantially eliminated or at minimum the parasite or infectious agent burden of the tissue is considerably reduced.

The term "body tissue" as used herein is to be understood to include "body fluid", packed red blood cells, packed white blood cells, platelets, cryo precipitate from blood plasma, other plasma proteins, skin, cornea, and other tissue from an animal or a human.

The term "body fluid" as used herein is to be understood to include whole blood, any formed elements of the blood, blood plasma, serum, fluids containing said components, fluids from plasmapheresis, plasma fibrinogen, cryo-poor plasma, albumin, gamma globulins, semen, and other fluids introduced or intravenously injected into the body of a patient or an animal using known administration techniques. The "body fluid" as used herein is to be understood to include body fluid prior to, or after, physical as well as chemical fractionation, separation or freezing.

The term "external" as used herein is to denote outside the animal or human body.

The method of the present invention provides for the external decontamination of body tissues containing infectious pathogenic biological contaminants such that the body tissues possess the desired therapeutic properties and viability as normal, untreated body tissues. Broadly, the method for treating body tissues to eradicate infectious pathogenic biological contaminants which may be present therein comprises:

(a) admixing an effective, non-toxic amount of a photoactive compound with the body tissue to produce a resulting body tissue, the photoactive compound having an affinity for infectious pathogenic biological contaminants in the body tissue such that the photoactive compound is selectively bound to such contaminants;

(b) passing the resulting body tissue under flow conditions through a cell assembly having a predetermined flow path or suspending the resulting body tissue in a solution; and (c) irradiating the resulting body tissue in the cell assembly as same travels along the flow path or suspends in the cell with an effective level of radiation for a prescribed period of time so that the radiation penetrates throughout the resulting body tissue in the irradiated path and exposes the photoactive-compound-bound contaminants to the radiation so as to eradicate such contaminants and produce a sterile body tissue.

Photoactive compounds which are selective for infectious pathogenic biological contaminants, and which can be used in the eradication of such contaminants in accordance with the present invention, must satisfy the following criteria:

(1) normal body tissues remain undamaged in an environment outside of a human body when subjected to a combined action of irradiation and the photoactive compound in levels effective to eradicate or destroy the infectious pathogenic biological contaminants present in such body tissues;

(2) the photoactive compound is preferentially bound to the infectious pathogenic biological contaminants either directly or indirectly by an antibody bridge or other linking molecule; and (3) upon irradiation, the photoactive compound eradicates or destroys the infectious pathogenic biological contaminants to which the photoactive compound has bound.

Photoactive compounds meeting the foregoing criteria comprise porphyrins or hematoporphyrins. Such compounds contain groups of pyrroles or substituted pyrroles combined in a specific pattern. The basic structural grouping consists of phlorin or a group of four pyrroles or combinations of pyrroles and substituted pyrroles combined into a larger ring structure. Two such rings are covalently bonded to form a pair of units each having four pyrrole groups or four groups at least some of which are pyrroles or substituted pyrroles. The resultant molecules have an absorption spectrum within the range of wavelengths of from about 350 nm and about 1200 nm, and more desirably from about 350 nm to about 700 nm.

The preparation and purification of photoactive compounds comprising porphyrin and hematoporphyrins is disclosed in U.S. Pat. No. 4,649,151; and certain of such photoactive compounds are commercially available from Johnson & Johnson as "Photofrin I TM" (Hpd) and "Photofrin II TM" (a compound containing approximately 90% dihematoporphyrin ether, DHE).

The molecular structure of at least a portion of such photoactive compounds which render such compounds useful in the practice of present invention is as follows:

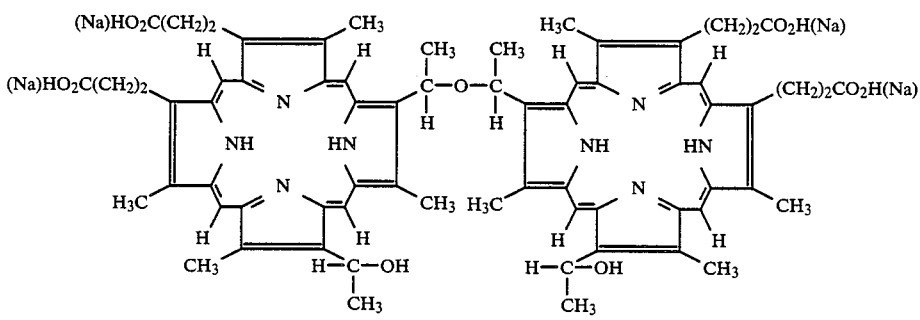

said molecules with said formula being fluorescent, photosensitizing, having the capability of selectively binding to said pathogenic biological contaminants, forming a high molecular weight aggregate with absorption peaks in the visible spectrum in water at approximately 365, 505, 537, 575, and 615 nanometers, absorption peaks in the infrared spectrum at approximately 3.0, 3.4, 6.4, 7.1, 8.1, 9.4, 12 and 15 microns, absorption peaks in carbon-13 nuclear magnetic resonance study at approximately 9.0, 18.9, 24.7, 34.5, 62, 94.5, 130-145, 171.7 ppm and possibly 118 and 127 relative to a 37.5 ppm resonance peak of dimethyl sulfoxide and additional absorption peaks in carbon-13 nuclear magnetic resonance study at approximately 27.9 ppm and 68.4 ppm relative to the resonance peak of tetramethylsilane in deuterated chloroform solvent; and at least 50 percent of the porphyrins in said mixture being of said molecule having said molecular formula.

The effective, non-toxic amount of the mixture of porphyrins admixed with the body tissue externally can vary widely, depending to a large degree on the amount of infectious pathogenic biological contaminants present or suspected to be present in the body tissue. However, to be effective the amount of the mixture of porphyrins utilized should be in excess of the amount of such contaminants to insure that sufficient mixture of porphyrins is present to bind all of the contaminants present in the body tissue. Generally, however, the amount of mixture of porphyrins admixed with the body tissue to satisfy the above requirement is from about 0.1 to about 50 micrograms of the mixture of porphyrins per milliliter of body fluid. Desirably, the amount of the mixture of porphyrins used is from about 2 to about 50 micrograms per milliliter of body fluid.

To eradicate the infectious pathogenic biological contaminants which have been bound to the photoactive compounds, the resulting mixture of body fluid and the photoactive compound is subjected to radiation, while maintaining the resulting mixture under flow conditions during exposure to the radiation.

Any suitable source can be employed to irradiate the photoactive-compound-bound contaminants provided such source produces sufficient radiation to activate the photoactive compound so as to eradicate or destroy such contaminants bound to the compound and sufficient energy to insure complete penetration of the radiation through the body fluid being treated, so that the treated body fluid is free of such contaminants. The operable source employed to irradiate the resulting fluid has a wavelength of from about 350 nm to about 1000 nm and an energy density of from about 0.1 J/cm$^2$ to about 50 J/cm$^2$. Desirably, the irradiating source has a wavelength from about 600 nm to about 700 nm with an energy density from about 1 to 20 J/cm$^2$. Suitable sources which satisfy such requirements are a Xenon 1000W light fitted with infra-red blocking filters and 630±10 nm band pass filter or a laser light source emitting radiation within (around 630nm) the absorption spectrum of the photoactive compound and having the desired energy density. Another suitable source is a quartz halogen lamp.

As previously stated, the resulting mixture of body fluids and the photoactive compound is subjected to radiation while being maintained under turbulent flow conditions. The turbulent flow conditions enhances the mixing of the photoactive compound with the body fluid to insure that the contaminants in the body fluid are sufficiently bound to the photoactive compound; and the turbulence further enhances exposure of the chemically bound contaminants to the desired level of radiation to insure eradication of such contaminants. However, the level of turbulence of the body fluid being treated must be maintained below a level where shearing of the body fluid or cells would occur.

Generally, in a flow cell system made up of a 40 cm long tubing with 0.5 mm internal diameter, a desired degree of turbulence can be achieved wherein the flow rate of the body fluid maintained at about 25 microliters per minute through the irradiation zone of a cell, i.e. the predetermined flow path of the cell. Further, to insure that the body fluid in such a flow cell is exposed to a sufficient level of radiation to eradicate the contaminants, the body fluids are exposed to a radiation density of about 5 J/cm$^2$.

As will become apparent, the desired exposure time can be readily controlled by the length of the flow path in combination with the flow rate of the body fluid through the flow path. However, care must be exercised to insure that irradiating of body fluid to eradicate or destroy the contaminants does not heat the body fluid to a temperature sufficient to destroy the viability of the purified body fluid.

For the extracorporeal treatment of the blood of a patient infected with infectious biological contaminants, a dosage from about 0.5 mg to about 40 mg of a mixture of porphyrins per kg of the body weight of the patient is commonly used. The mixture of porphyrins can be administered to the patient either by oral or intravenous route. The mixture of porphyrins can be given from about one hour to about one week prior to the start of irradiating the blood removed from the patient's body. Generally, the blood that contains the mixture of porphyrins bound to the infectious biological contaminants is removed from the body of the patient and circulated through a flow cell where said blood is irradiated with a light source having a wavelength of about 600 to 700 nm. The energy density most often used to irradiate the blood in the flow cell is from about 1 $J/cm^2$ to about 50 $J/cm^2$.

Alternatively, the patient's blood that is infected with infectious biological contaminants is removed from the patient's body and then admixed with a sterile saline solution containing an effective amount of a mixture of porphyrins to bind to all the infectious contaminants. The saline solution containing the mixture of porphyrins is added at a rate that will maintain the concentration of the mixture of porphyrins in the resulting fluid to be from about 0.1 to about 50 micrograms per milliliter of the infected blood. The preferred concentration, however, is from about 2 to about 50 micrograms per milliliter of infected blood. The resulting fluid is then irradiated in the flow cell assembly as the resulting fluid passes through the flow path. The operable light source for irradiation has a wavelength of about 600 to 1000 nm, although the preferred wavelength range is from about 600 to 700 nm. The operable energy density that can be used to irradiate the resulting fluid in the flow cell is from about 1 to 50 $J/cm^2$, but the preferred range is from about 1 to 20 $J/cm^2$.

Due to diapedesis, a natural phenomenon in which some lymphocytes pass through the intact walls of blood vessels and mix with other tissue fluids, not all lymphocytes will be available, at one time, for the extracorporeal treatment. Accordingly, the patient undergoing such extracorporeal treatment has to be subjected to a series of extracorporeal treatments with an interval of a few days ranging from 2 to 7 days. The duration of one extracorporeal treatment can range from about 3 to about 10 hours.

A pump is usually not required for the operation of extracorporeal treatment. At a systolic blood pressure of 130 to 170 mm Hg, the blood can flow through a flow cell at a rate of about 80 to 140 ml/min through a channel of typical cross-section of 0.7×100 mm with a length of about 150 to 200 cm. The flow cell for this procedure can be constructed to contain a total of about 120 ml of blood.

As discussed above, there is currently no cure for AIDS. Without an effective treatment, AIDS victims live, on the average, about 2 years after diagnosis. It is only logical that if the viremea of an AIDS victim can be reduced, such a victim would have a better chance of staying alive longer, or at least the life in this victim can be improved. The extracorporeal photochemical treatment of infected blood from an AIDS patient can fulfill such a goal because the method described herein has been shown to eradicate human immunodeficiency virus which causes AIDS.

Where the body tissue is not in fluid form, said tissue is excised from the donor as a thin layer that is translucent to light and is then suspended in a physiologically acceptable saline solution containing an effective, non-toxic amount of the photoactive compound. The resulting suspension is then subjected to radiation while maintaining the resulting suspension under gentle aggitation during exposure to the radiation. The gentle aggitation would enhance the mixing of the photoactive compound and the tissues suspended in the solution to insure that the infectious biological contaminants in the body tissues are sufficiently bound to the photoactive compound; and the gentle aggitation further enhances exposure of the chemically bound contaminants to the desired level of radiation to insure irradication of such contaminants. The gentle aggitation can be achieved by placing the entire irradiation assembly in a laboratory shaker. Thus, the cell assembly can be gently aggitated while the body tissues suspended in sterile solution are being irradiated.

The operative amount of the mixture of porphyrins to be added to the suspension of body tissue in a physiologically acceptable saline solution is from about 0.1 to about 50 micrograms per milligram of the suspended body tissue. Deisrably, however, the amount of the mixture of porphyrin added is from about 2 to 50 micrograms per milligram of the suspended body tissue. The source employed to irradiate the resulting suspension has a wavelength of from about 350 nm to about 700 nm and an energy density of from about 0.1 $J/cm^2$ to about 20 $J/cm^2$. Desirably, the irradiation source has a wavelength from about 600 nm to about 700 nm with an energy density from about 1 to about 20 $J/cm^2$.

As previously set forth, the method of the present invention provides an economical and efficient means for externally eradicating infectious pathogenic biological contaminants from body tissues so that the likelihood of a person becoming infected as a result of a transfusion or transplantation is substantially eliminated. The contaminants which can be effectively eradicated from a body fluid using the present invention are the enveloped viruses, other microorganisms, including other parasites and bacteria. The term "enveloped virus" in all cases but one is understood to be a virus of which is encased within a modified host cell membrane, except for the Pox-virus which produce ®their own envelope. Typical of such enveloped viruses are: Cytomegalovirus, Herpes simplex virus, Pox virus, human immunodeficiency virus, Epstein-Barr virus, and others as set forth in Table I.

TABLE I

The following are enveloped viruses as divided into Family and common species or genus:

| Family | Common Species or Genus |
|---|---|
| Herpesviridae | Human herpes simplex virus types 1 and 2 |
| | bovine mammillitis virus |
| | herpes B virus of monkeys |
| | pseudorabies virus |
| | equine rhinopneumcntis virus |
| | varicella-zoster virus |
| | human cytomegaloviruses |
| | murine cytomegaloviruses |
| | Epstein-Barr virus |
| | Baboon herpes virus |
| | Chimpanzee herpesvirus |
| | Marek's disease herpes virus |
| | Hinze virus |
| | Turkey herpes virus |
| | Herpesvirus ateles |

TABLE I-continued

The following are enveloped viruses as divided into Family and common species or genus:

| Family | Common Species or Genus |
|---|---|
| | Herpesvirus saimiri |
| | infectious bovine rhinotracheitis virus |
| Iridoviridae | African swine fever virus |
| | Frog virus group (Ranavirus) |
| | Iridovirus |
| | Chloriridovirus |
| Poxviridae | vaccinia virus |
| | smallpox virus |
| | cowpox virus |
| | monkeypox virus |
| | buffalopox virus |
| | camelpox virus |
| | ectromelia of mice virus |
| | rabbitpox virus |
| | Orf virus |
| | virus of milker's node |
| | avipoxvirus |
| | sheep pox virus |
| | goat pox virus |
| | lumpy skin disease (Neethling) virus |
| | myxoma virus of hares |
| | fibroma viruses of rabbits |
| | fibroma viruses of squirrels |
| | swinepox virus |
| | Yaba monkey virus |
| | molluscum contagiosum virus |
| Hepadnaviridae | human hepatitis B virus (HBV) |
| | woodchuck hepatitis virus |
| | ground squirrel hepatitis virus |
| | duck hepatitis virus |
| Orthomyxoviridae | Influenza virus, types A, B, and C |
| Paramyxoviridae | Newcastle disease virus of fowl |
| | human parainfluenza viruses |
| | Sendai virus |
| | mumps virus |
| | paramyxoviruses |
| | measles virus |
| | rinderpest virus of cattle |
| | canine distemper virus |
| | peste-des-petits-ruminants virus of sheep and goats |
| | respiratory syncytial virus of man |
| | bovine respiratory syncytial virus |
| | pneumonia virus of mice |
| Rhabdoviridae | rabies virus |
| | vesicular stomatitis virus of: horses, cattle and swine |
| | chandipura virus |
| | lyssavirus |
| | duvenhage virus |
| | Lagos bat virus |
| | mokola virus |
| Bunyaviridae | bunyavirus (Bunyamwera, Bwamba, California, Capim, Guam, phlebovirus koongol, patois, simbu and tete viruses) |
| | sandfly fever virus |
| | Rift Valley fever virus of sheep and ruminants |
| | Nairovirus |
| | Crimean-Congo hemorrhagic fever viruses |
| | Uukuvirus |
| | Uukuniemi virus |
| | Hantaan virus |
| | Korean hemorrhagic fever virus |
| Filovirdae | ebalo virus |
| | Marburg virus |
| Nodaviridae | Nodamura virus |
| Togaviridae | Alphaviruses |
| | aura virus |
| | Chikungunya virus |
| | eastern equine encephalitis virus |
| | getah virus |
| | mayaro virus |
| | middleburg virus |
| | mucamba virus |
| | ndumu virus |
| | O'Nyong-nyong viru |
| | pixuna virus |
| | ross river virus |
| | semliki forest virus |
| | sindbis virus |
| | una virus |
| | Venezuelan equine encephalitis virus |
| | western equine encephalitis virus |
| | Whataroa virus |
| | rubella virus |
| | mucosal disease virus |
| | border disease virus |
| | hog cholera virus |
| Flaviviridae | flavivirus |
| | Brazilian encephalitis virus |
| | Bussuquara virus |
| | dengue virus |
| | iiheus virus |
| | Isreal turkey meningoencephalitis virus |
| | Japanese B encephaitis virus |
| | kunjin virus |
| | Kyasanur forest disease virus |
| | langat virus |
| | louping ill virus |
| | modoc virus |
| | Murray valley encephalitis virus |
| | ntaya virus |
| | omsk hemorrhagic fever virus |
| | powassan virus |
| | St. Louis encephalitis virus |
| | spondwnei virus |
| | tick-borne encephalitis |
| | Uganda S virus |
| | US bat salivary gland virus |
| | wesselsbron virus |
| | west nile fever virus |
| | yellow fever virus |
| | zika virus |
| | european tick-borne encephalitis |
| | far eastern tick-borne encephalitis virus |
| | Russian tick-borne encephalitis |
| Retroviridae | type C oncovirus group |
| | type B oncovirus group |
| | type D retrovirus group |
| | avian complex leukemia virus |
| | Rous sarcoma virus |
| | murine complex leukemia virus |
| | mouse sarcoma virus |
| | murine mammary tumor virus |
| | feline complex leukemia virus |
| | feline complex sarcoma virus |
| | wooly monkey sarcoma virus |
| | Gibbon leukemia virus |
| | mason-Pfizer virus |
| | hamnster leukemia virus |
| | rat leukemia virus |
| | bovine lymphoma virus |
| | human T cell leukemia viruses types 1 and 2 etc. |
| | spumavirinae: syncytial and foamy viruses of humans, monkeys, cattle, cats |
| | visna virus of sheep |
| | Maedi virus |
| | progressive pneumonia viruses of sheep |
| | *human immunodeficiency viruses (includes HTLV III/LAV) |
| | HIV, HTLV IV, LAV-2, STLV-III$_{AGM}$ |
| Arenaviridae | Junin virus |
| | lassa virus |
| | machupo virus |

TABLE I-continued

The following are enveloped viruses as divided into Family and common species or genus:

| Family | Common Species or Genus |
|---|---|
| | pichinde virus |
| | lymphocytic choricmeningitis virus |
| | lassa fever virus |
| | pichinde virus |
| | arenavirus |
| Other virus-like agents viroids-prions | kuru virus |
| | Creutzfeldt-Jakob disease virus |
| | scrapie virus |
| | transmissible mink encephalopathy |
| | Aleutian disease of mink |

*NOTE:
under Retroviridae
HTLV III, human T-lymphotropic virus type III
LAV, Lymphadenopahty virus
HIV, hmman immunodeficiency virus
STLV III$_{AGM\ simina\ T\text{-}lymphotropic\ virus\ type\ III}$
HTLV IV, human T-lymphotropic virus type IV
HTLV III and LAV are now usually referred to as HIV Microorrganisms, parasites and bacteria which can be effectively eradicated by the method of the present invention include: *Plasmodium vivax, P. malariae, P. falciparum, P. ovale,* and *Trypanosoma cruzi; Bacillus subtilis,* and *Streptococcus faecalis.*

In order to more fully describe the method for eradicating infectious pathogenic biological contaminants from body fluids in accordance with the present invention, reference is now made to FIG. 1 through FIG. 10 of the drawings wherein schematic representations of cell assemblies useful in the practice of the invention are set forth.

In irradiating blood or blood products to achieve photodynamical killing of infectious pathogens with the preferred embodiment, the container with uniform thickness of surfaces containing th ®flowing product is illuminated with light of essentially uniform intensity and of appropriate wavelength to initiate photosensitization. With such uniform irradiation, all units of blood or blood products flowing between the two boundary surfaces receive essentially the same incident light fluence. In this way, fluid flow and illumination conditions, demonstrated experimentally to result in killing of the pathogen, can be accurately reproduced.

Similarly, the irradiation cell for the irradiation of body tissues suspended in a physiologically acceptable saline solution has boundary surfaces of uniform thickness. The irradiation cell assembly is also illuminated with light of essentially uniform intensity and of appropriate wavelength to initiate photosensitization. With such uniform irradiation, all areas of the body tissues receive essentially the same incident light fluence. Hence, the results obtained can be accurately reproduced.

FIG. 1 shows a schematic diagram of a flow cell used in the original experiments. Whole blood or other body fluid was infused via a syringe driven by an infusion pump. The blood or body fluid was constrained to flow through a flexible transparent plastic tube, 11, which was looped along the planar surface of a 2 in. ×2 in. area of transparent glass slide, 12, which served to support the tube in a plane perpendicular to the irradiating light beam. The tube was attached to the glass slide 12 by epoxy glue shown as 14. Tube diameter was 0.05 cm and the length of the tube illuminated was 40cm. Irradiation was essentially uniform with irradiance $I_o$ of $1.04 \times 10^{-2}$ w/cm$^2$ at 630±5 nm wavelength. Flow rate of body fluid was $9.8 \times 10^{-4}$ cm$^3$/min. The flow time for each unit of volume element of body fluid within the illuminated region was about 8 minutes. Irradiation of the 2×2 in. planar area occupied by the looped flow tube for the 8 min. flow time resulted in a fluence of $E_o = 5$ J/cm$^2$ delivered to the planar area of the looped tube.

Figure 2:
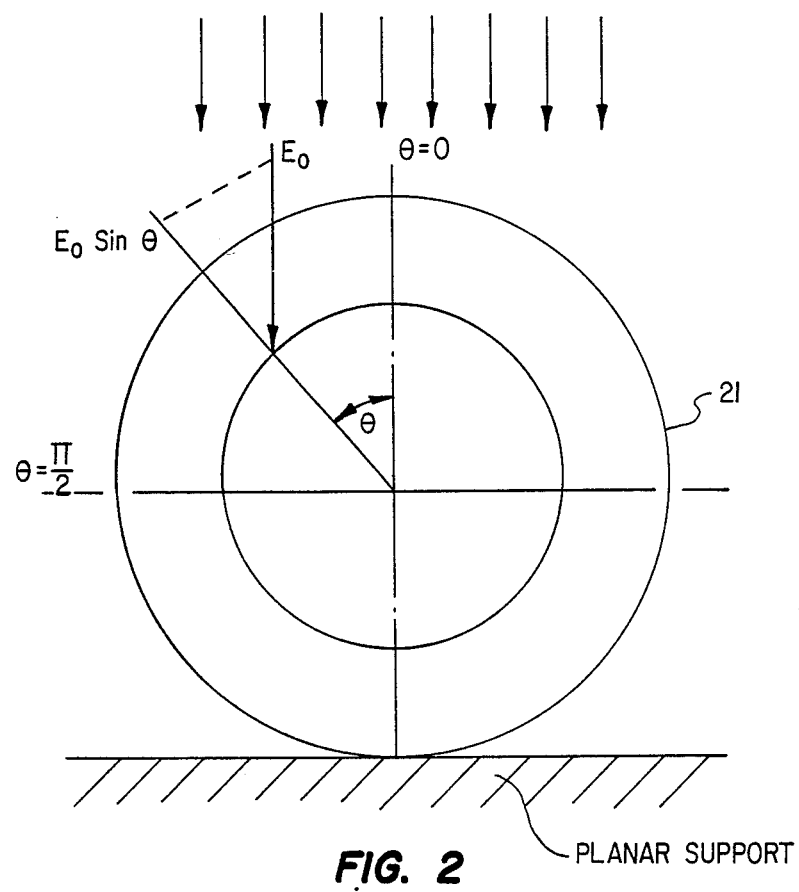
FIG. 2 is an enlarged cross-sectional view of the flexible transparent plastic tube of FIG. 1

FIG. 2 shows the enlarged cross sectional view of the flow tube, 21, sitting on a planar support with the incident light, Io, coming in along the direction as shown by arrows.

The corresponding average fluence $<E>$ over the hemicylindrical surface of flow tube is obtained by the integral:

$$<E> = \frac{2 E_o \int_o^{\pi/2} \sin\theta d\theta}{2 \int_o^{\pi/2} d\theta} = \left(\frac{2}{\pi}\right) E_o$$

where ($E_o \sin\theta$) is the component of $E_o$ perpendicular to the hemicylindrical surface at the point defined by the angle $\theta$ between the radius vector to the point and the direction antiparallel to the direction of the incident light.

Figure 3:
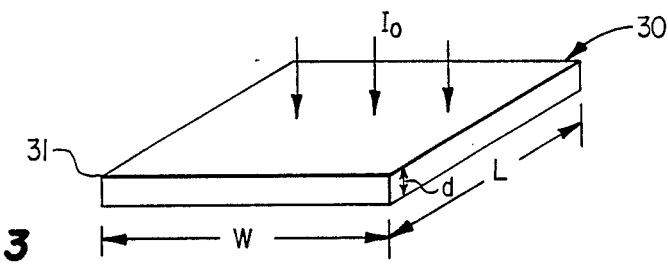
FIG. 3 is a perspective view of the irradiation cell being irradiated from the top of the cell.
Figure 3A:
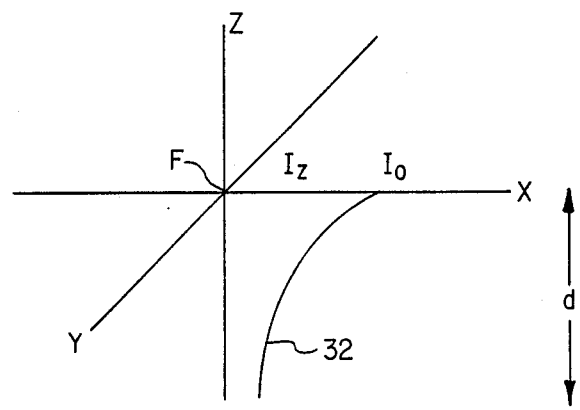

Although useful in demonstrating the efficacy of dihematoporphyrin ether (DHE) based photodynamical killing of infectious pathogens in blood or other body fluid, the embodiment described above is limited in at least two ways. Firstly, throughput rate is severely limited. Secondly, due to variation in irradiance with angle $\theta$ and due to light absorption and scattering, light exposure at various depths below the illuminated cylindrical surface of the flowing fluid volume element varies with positions along the diameter of the tube. Uniformity of light intensity with depth, and hence, calculation and control of dosimetry, would be improved if the blood or other body fluid would flow as a plane layer of uniform thickness, d, which is exaggerated in the drawing, with the uniform surface illumination as shown in FIG. 3. When it is the body fluids that are to be treated photochemically, the cell 30 would function as a flow cell to direct the flow of body fluids. If, on the other hand, it is the thin layer of body tissue to be subjected to photochemical treatment, the cell would serve to hold the suspension of body tissue in a physiologically suitable saline solution.

Still referring to FIG. 3, the uniform width of the irradiation cell 30 is denoted by W, while the uniform length of the cell is L. In this scheme, the incident light $I_o$ and the falloff of light intensity $I_z$ with depth along Z axis is everywhere uniform on any plane of constant depth from the irradiated surfaces. Additionally, flow rate within such a layer with much larger cross-sectional area than the previously used tubing is considerably enhanced.

FIG. 3-a shows the decrease of the intensity of unidirectional irradiation as the irradiating light travels along the depth, d, of the irradiation cell 30, as depicted in FIG. 3. The geometry of the irradiation is graphically illustrated as a three-dimensional rectangular coordinate system (X, Y, Z). The two horizontal axes are X and Y, while the vertical axis is Z. The depth, d, of the irradiation cell 30 is defined by the Z axis; the width, W, of the irradiation cell 30 is defined by X axis; and the length, L, of the irradiation cell 30 is defined by Y axis. The origin F represents point 31 at the upper left hand corner of the irradiation cell 30.

Referring still to FIG. 3-a, the Z component, $I_Z$, of the irradiating light $I_o$, as represented by line 32, decreases in intensity as the light travels through the thickness d of the cell 30. The decrease in intensity is a function of the distance of the path travelled by the irradiation, as is shown by line 32 which approaches zero as the distance travelled by light along the thickness d increases.

Figure 4:
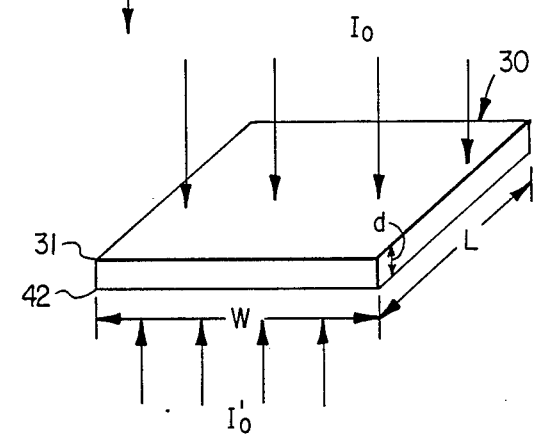
FIG. 4 is a perspective view of the irradiation cell being irradiated from both the top and the bottom of the cell.

FIG. 4 shows the irradiation cell 30 being irradiated from both vertical directions. The irradiation cell 30 could either be a flow cell directing the flow of body fluids or a cell housing a suspension of body tissues in a physiologically acceptable saline solution. The uniform irradiation from the top of the cell assembly, as shown by arrows pointing downward, along the width d, is represented by Io; while the uniform irradiation from the bottom of the cell assembly, as shown by arrows pointing upward along the width d, is represented by $I'_o$. The uniform thickness of the irradiation cell 30 is represented by d and is exaggerated in the diagram. The width of the cell 30 is represented by W, while the length of the cell 30 is represented by L. Both L and W are again of uniform dimensions in this embodiment.

FIG. 4-a graphically depicts the geometry of the double irradiations as two three-dimensional rectangular coordinate systems, (X, Y, Z) and (X', Y', Z'). The four horizonal axes are X, Y, X', and Y'. The two vertical axes are Z and Z'. The depth d of the irradiation cell 30 is represented by the two vertical axes, Z and Z'; the width W of irradiation cell 30 is represented by horizontal axes X and X'; and the length L of the irradiation cell 30 is represented by horizontal axes Y and Y'. The origins F and F' represent points 31 and 42, respectively, in FIG. 4.

As is shown in FIG. 3-a, the Z component, $I_z$, of the irradiation Io decreases in intensity as the light travels through the thickness d of the irradiation cell 30. This decrease in intensity is depicted by line 32 which approaches zero as the distance travelled by light along the thickness d increases.

Figure 4A:
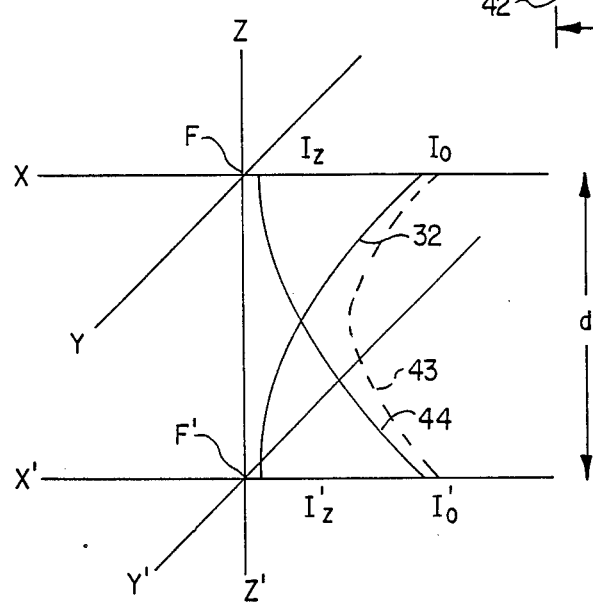

Likewise, the Z' component, $I_z'$, of the irradiation $I'_o$ decreases in intensity as the light travels through the thickness d of the irradiation cell 30. The change in intensity is depicted by line 44 which approaches zero as the distance travelled by light along the thickness d increases. Still referring to FIG. 4a, when the irradiation cell 30 is irradiated from both directions by uniform light beams Io and $I'_o$, the total intensity of Z component obtained is $I(z+z')$ which is equal to the summation of Iz and Iz' as represented by the broken line 43. The intensity of light represented by line 43 is, at all times, greater than the intensity represented by either line 32 or line 44 alone. Consequently, when the irradiation cell 30 is irradiated from two opposite directions, the resultant light intensity obtained in the cell 30 is greater than the intensity obtained when the cell 30 had been irradiated from one direction only.

Figure 5:
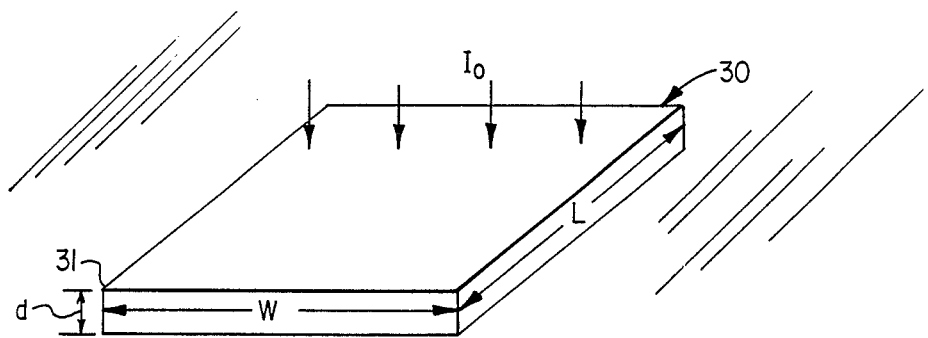
FIG. 5 is a perspective view of the irradiation cell being supported on the bottom by a reflecting mirror surface while the cell is being irradiated from the top of the cell.
Figure 5A:
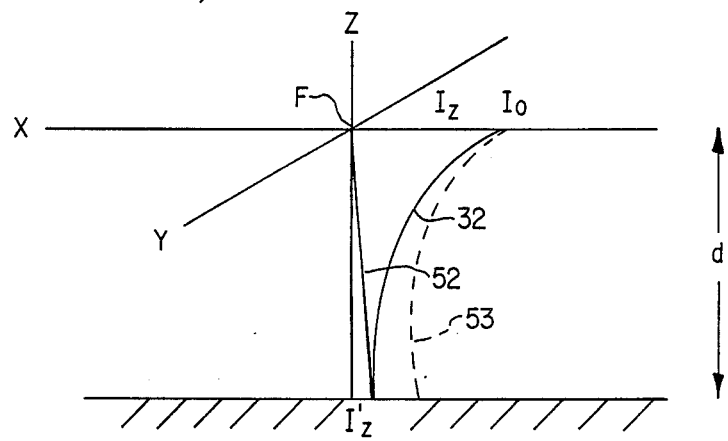

FIG. 5 illustrates the irradiation cell 30 being supported by a reflecting mirror surface while the cell is being irradiated by a uniform light beam Io from the opposite direction as shown by the arrows. As in FIG. 4, the irradiation cell 30 could either be a flow cell directing the flow of body fluids or a cell housing a suspension of body tissues in a physiologically acceptable saline solution. The uniform thickness of the irradiation cell 30 is represented by d and is exaggerated in the diagram. W represents the uniform width of the irradiation cell 30, while L represents the uniform length of the irradiation cell 30.

FIG. 5-a graphically depicts the geometry of the irradiation and its reflection from the supporting reflecting mirror as a three-dimentional rectangular coordinate system (X, Y, Z). The two horizontal axes are X and Y, while the vertical axis is Z. The depth, d, of the irradiation cell 30 is defined by Z axis; the width, W, of the irradiation cell 30 is defined by X axis; and the length, L, of the irradiated cell 30 is defined by Y axis. The origin F represents point 31 of the irradiation cell 30.

FIG. 5-a shows the Z component, Iz, of the irradiation $I_o$ decreases in intensity as the light travels through the thickness d of the irradiation cell 30. This decrease in intensity is depicted by line 32 which approaches zero as the distance travelled by light along the thickness d increases.

The Z component of this reflects light, $I_{z''}$, approaches zero as the reflection travels through the thickness d of the irradiation cell 30.

Still referring to FIG.5-a, with the introduction of the reflecting mirror as a support for the irradiation cell 30, however, the total intensity along Z component obtained in $I(Z+Z'')$ which is equal to the summation of Iz and Iz'' as represented by the broken line 53. The intensity of light represented by line 53 is greater than the intensity represented by either line 32 or line 52 alone. Consequently, the introduction of a reflecting mirror also enhances the light intensity obtained in the irradiation cell 30.

Figure 6:
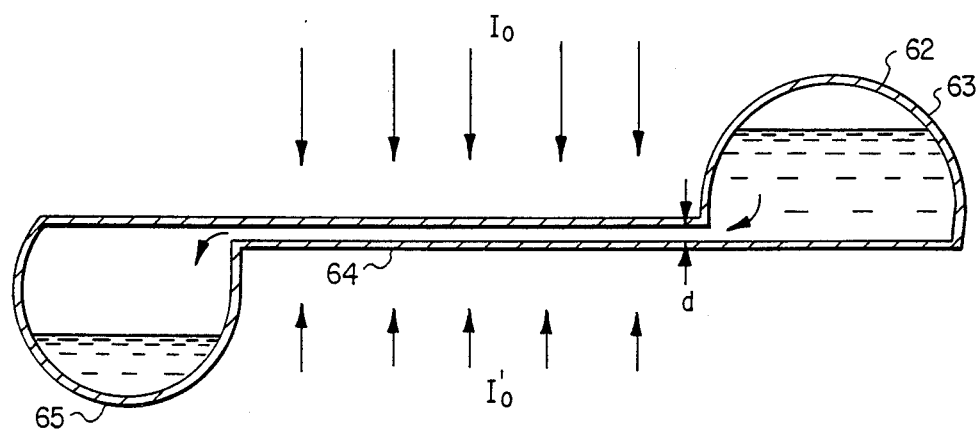
FIG. 6 is a longitudinal sectional view of another embodiment of the flow cell.

FIG. 6 shows the longitudinal sectional view of another embodiment of the flow cell. The flowing layer of blood or body fluid is confined within a transparent, thin walled, (62), flexible, flat tubular volume, 64, connecting a collection bag 63, and a receptacle bag 65. After the body fluid flows from the collection bag 63 through the flat tubular space 64 where the body fluid is illuminated, the body fluid is received and ultimately stored in the receptacle bag 65. Representative dimensions for the flowing layer in the illuminated zone are width=5 cm; length =40 cm; thickness d=0.05 cm. For this configuration, representative treatment conditions include a total incident light intensity of $1.04 \times 10^{-1}$ w/cm$^2$ at 630±5 nm wavelength divided equally over both lateral 40×5 cm surfaces ($5.02 \times 10^{-2}$ w/cm$^2$ to each) combined with a flow rate of about 24.96 cm$^3$/min. This combination led to a total incident fluence over the two surfaces of an elemental volume of 5 J/cm$^2$. this light dosage with a Photofrin II ™ concentration centration of $2.5 \times 10^{-6}$ gm/cm$^3$ has been demonstrated to effectively kill envelope viruses and other infectious pathogens.

Figure 7:
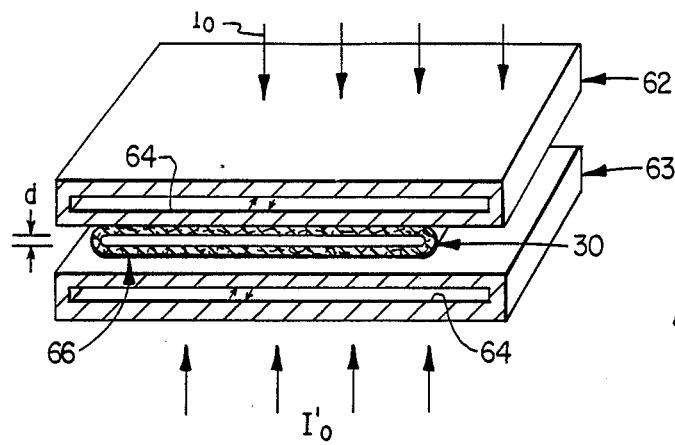
FIG. 7 shows a perspective view of the irradiation cell sandwiched between two transparent flat plattens while the assembly is being irradiated from two opposite directions, top and bottom, of the cell.

In order to maintain uniform thickness, d, in the irradiation cell 30, the cell 30 can be constrained between two transparent flat plattens, 62 and 63, held apart at the correct distance with a spacer as shown in FIG. 7. These plattens can be hollow to allow the circulation of a heat exchange medium, 64, to cool the irradiated body tissue, either as a flowing body fluid or as a suspension of body tissue, in a physiologically acceptable saline solution. In this way, deleterious photothermal effects such as red cell lysis potentially resulting from absorption of incident light by hemoglobin can be minimized while maintaining a high incident light fluence. The whole system can be illuminated with light sources entering the system from two opposite directions, as depicted by $I_o$ and $I'_o$. Alternatively, the surface of one of the flat plattens can be made up of reflective mirror to reflect the single unidirectional irradiation coming in from the opposite direction.

Illumination from two opposite directions, instead of just one, helps to overcome effects of light intensity falling off with penetration depth into the flowing body fluid due to light absorption and scattering (FIG. 4-a). Suitable light sources for illumination include lamp and laser sources. Especially suitable is a xenon, quartz halogen or metal vapor lamp with output energy containing the wavelength range of 630±5 nm. These lamps are available in long straight small diameter tubular shape; hence they can be easily arranged in a co-parallel fashion in two planes which are parallel to the flowing blood layer surfaces to illuminate these surfaces (FIG. 8).

Figure 8:
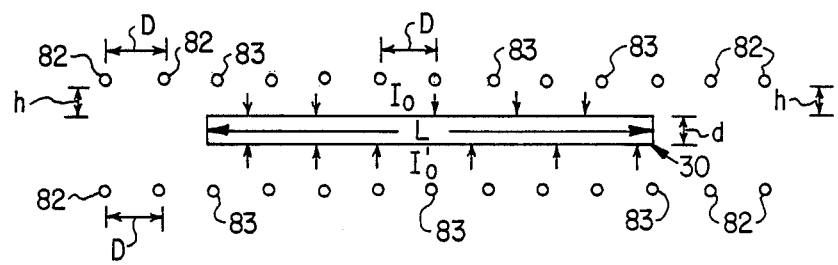
FIG. 8 shows the longitudinal sectional view of the irradiation cell surrounded on the top and bottom with two arrays of tubular lamps which are depicted cross-sectionally as small circles.

FIG. 8 shows the longitudinal sectional view of the irradiation cell 30 sandwiched between two arrays of long and tubular lamps, 82 and 83, to give a uniform irradiation over both surfaces of the flow cell 30 along the length L. The cross-sectional view of the light sources, 82 and 83, are drawn as small circles in the picture. The irradiation cell 30 could either be a flow cell directing the flow of body fluids or a cell housing a suspension of body tissues in a physiologically acceptable saline solution.

These long tubular lamps, 82 and 83, each parallel to the other, were arranged with their length parallel to the width of the cell 30. When the distance D between the adjacent lamps was equal to the distance h between the plane containing the array of lamps and the illuminated surface of the irradiation cell 30, the mean variation in light flux along the layer length L of the irradiation cell 30 was less than approximately 2.5%, provided the lamp array extends beyond the length of the irradiation cell 30 by at least 2 additional lamps 82 at both ends. The result is graphically depicted in FIG. 9 as a two-dimensional coordinate system (X, Y).

Figure 9:
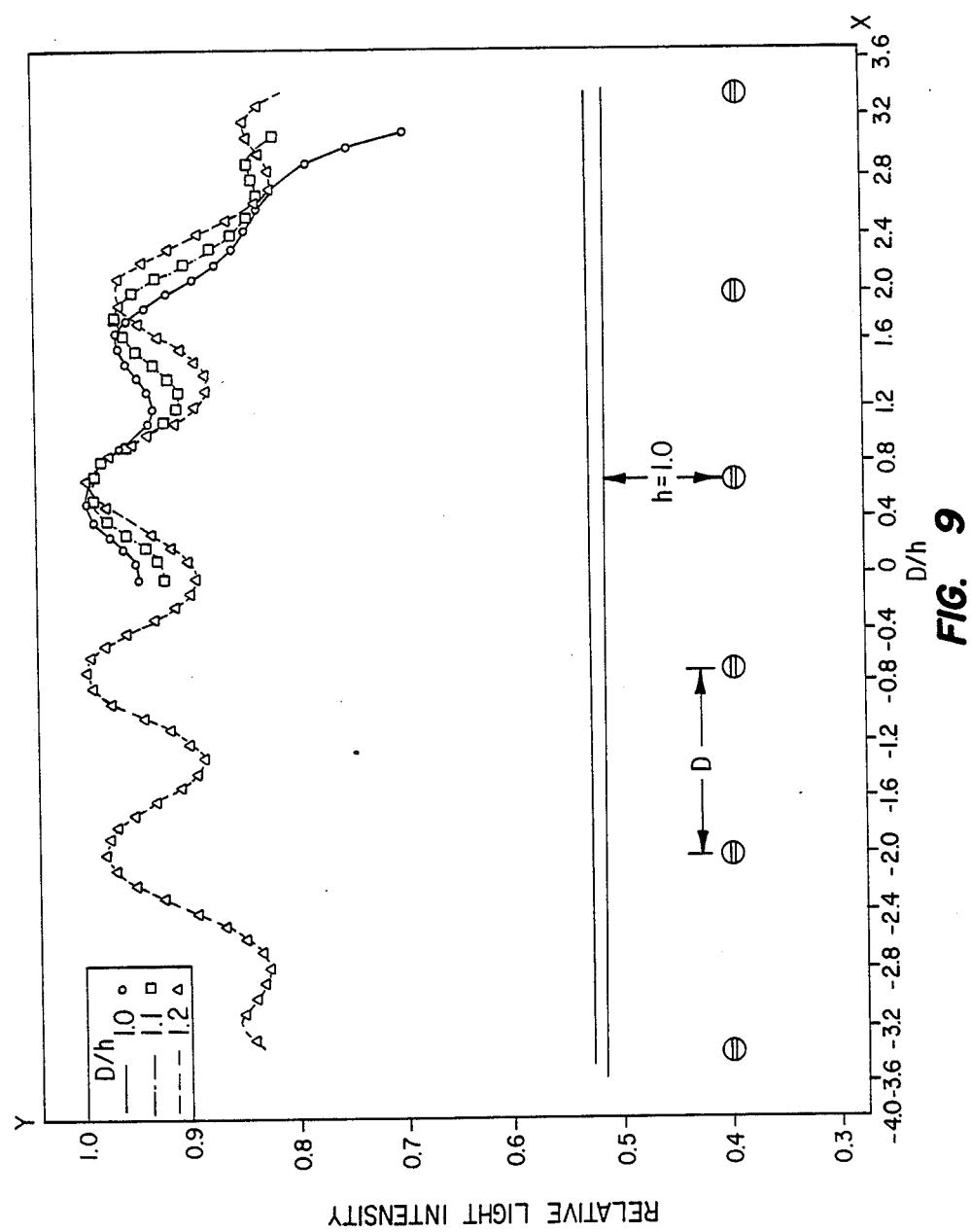
FIG. 9 is a plot of normalized relative light intensity vs. the ratio of distance D with respect to distance h. Distance D is the spacing between two adjacent lamps, while distance h is the separation between the plane containing the array of lamps and the illuminated surface of the irradiation cell.

In FIG. 9, the horizontal axis denotes the ratio $D/h$. D is the spacing between two adjacent lamps; while h is the separation between the plane containing the array of lamps and the illuminated surface of the irradiation cell. The vertical Y axis denotes the relative light intensity. In this particular graph, the distance h was normalized to a value of 1. The lamps are parallel to each other and are arranged in a plane parallel but along the width of the irradiation cell. A total of six lamps, equally spaced from one another at a distance D, were used. The width of the tubular lamp was roughly one-tenth the value of h. Relative to distance h, which was normalized to a value of 1, the separation between two adjacent tubular lamps was 1 (denoted by small circles in the graph), 1.1 (denoted by small squares in the graph) or 1.2 (denoted by small triangles in the graph). This relative separation was plotted against the variation in light flux in FIG. 9. The solid line, formed by joining small circles, represent the variation in light flux when the tubular lamps were separated from one another by a distance equal to h. The solid line shows that the mean variation in light flux among the four internal lamps, hence along the layer length of the flow cell, was less than 2.5%.

Figure 10:
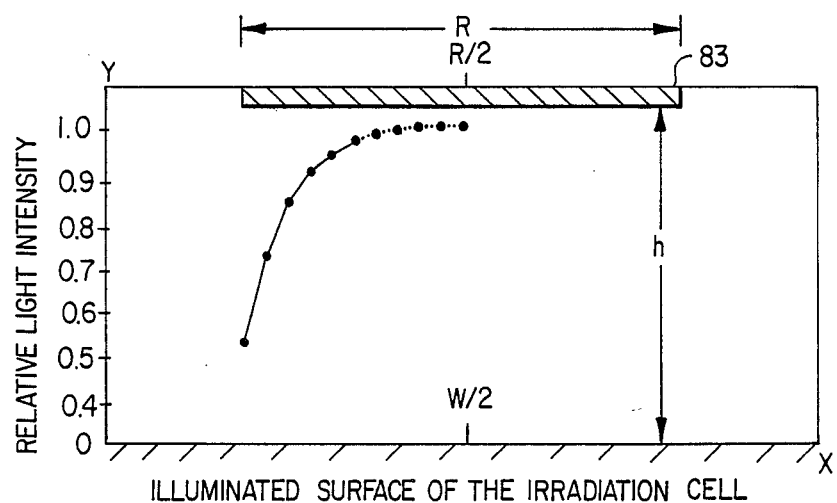
FIG. 10 is a plot of normalized relative light intensity along the length of the tubular lamp. The longitudinal sectional view of the lamp is shown on top of the diagram.

FIG. 10 is a plot of relative light intensity along the length R of the tubular lamp 83. The vertical Y axis of the two-dimensional rectangular coordinate represents the relative light intensity with the maximum intensity arbitrarily assigned a unit valve of 1. The horizontal X axis represents the illuminated surface of the irradiation cell which was parallel to the tubular lamp 83. Again the distance between the plane containing the lamps and the surface of the irradiation cell is h. It can be seem from FIG. 10 that the light intensity was at it maximum, arbitrarily assigned a unit value of 1, around the midpoint R/2 along the length R of the tubular lamp 83. The light intensity gradually fell off toward the two terminal of the tubular lamp 83.

Thus, when the length L of each tubular lamp was twice the width W of the irradiation cell and placed with its midpoint L/2 above the midpoint W/2 of the layer width, the mean variation in light intensity with width of the irradiation cell was less than 1.6%.

In order to achieve an essentially uniform total irradiance of $1.04 \times 10^{-1}$ w/cm$^2$ over the two surfaces of the irradiation cell, $5.02 \times 10^{-2}$ w/cm$^2$ must be provided to each side. When an area with the width of 10 cm and the length of 40 cm was irradiated with 4 lamps spaced at 2 cm apart and a lamp length of 10 cm, 24.10 watts output per lamp bank was obtained. Using a total of 24 lamps per surface resulted in a requirement of 1.04 watts output lamp emitting the energy in the range of 630±5 nm. This arrangement gave 10.04 watts per surface incident on the flowing body fluid in the flow cell. Dichroic lamp coatings and/or platten coatings as well as infra-red absorbing filters could be used to ensure no thermal damage to optics, suspended body tissue, or flowing body fluid would take place.

It should be emphasized that all the procedures described above are to be carried out in a closed system to prevent the exposure of the body tissues to the unsterile environment.

In order to more fully describe the present invention the following examples are setforth. However, it is to be understood that the examples are for illustrative purposes and are not to be construed as limiting the scope of the invention as defined in the appended claims.

EXAMPLES

Photo-Irradiation Of Human Blood

Photo-irradiation of human blood was performed in a prototype instrument as described in FIG. 1. The human blood, was pumped using a syringe pump, through narrow bore plastic tubing attached to a small glass plate with epoxy adhesive. The tubing followed a serpentine route across the plate. The blood was pumped through the tubing at a rate of 22.6 microliters per minute. Normal blood samples were divided into 4 separate aliquots. Aliquot 1 was pumped through the cuvet following pretreatment with Photofrin II TM (from Johnson and Johnson; containing approximately 90% of pure dihematoporphyrin ether (DHE)) and without photoirradiation. Aliquot 2 was treated in an identical fashion except that it was photo-irradiated as it flowed through the cuvet. Aliquot 3 was incubated with Photofrin II TM for 25 minutes then passed through the flow cell without photoirradiation. Aliquot 4 was incubated for 25 min. with Photofrin II TM then pumped through the flow cell as before except the aliquot was photo-irradiated. Thus, aliquots 1 through 3 are appropriate controls for aliquot 4.

Blood samples were obtained from four normal healthy individuals, (LM, JEL, LH, RB). One blood sample (HS) was pretreated with *Herpes simplex* virus Type 1 prior to irradiation while two samples (BL and BD) were from patients suffering from acquired immune deficiency syndrome (AIDS).

Samples obtained from patients found positive to the human immunodeficiency virus (HIV) antibody were divided into two aliquots and treated like aliquots 1 and 4 described above.

Fibrinogen assays were performed according to the procedure published by K. Jacobson (Scand. J. Clin. Lab. Med. 7: 7, 1955), using commercial reagents (American Dade). Osmotic fragility was performed using commercial reagents according to the method described by Dacie and Lewis (J.V. Dacie & S.M. Lewis, Practical Haematology Churchill Livingston, 1975). Sugar water lysis test was performed according to the method described by Dacie and Lewis (Practical Haematology). Prothrombin time was measured using commercial reagents (American Dade) using the automated coagulation instrument MLA700 (Medical Laboratory Automation). The activated partial thromboplastin time (APTT) was performed using commercially available reagents (American Dade) according to methods described by that company using the MLA700 coagulaton instrument. Electrolytes sodium potassium calcium were measured using the Nova 6 electrolyte analyser which employs ion specific electrodes according to methods established by the manufacturer. Glucose was measured in plasma samples using the Beckman Glucose Analyser Model 2 according to procedures recommended by Beckman Instruments Corp. Blood counts were measured using the fully automated machine Coulter S PLUS IV (Coulter Electronics). Differential counts were performed manually using a blood smear prepared by the wedge technique on a glass slide and the blood was then stained with Wright's Stain. Oxygen dissociation was performed on the Aminco Hem-0-Scan according to methods described by that manufacturer. Serum protein electrophoesis was performed according to the method described by Helena Laboratories on equipment manufactured by them. All the above methods are in routine use in these laboratories. The results are tabulated in Tables II through IV, followed by listings of abbreviations used in the Tables.

TABLE II

RESULTS: Human Blood From Normal, Healthy Volunterrs

| Donor | LM | LM | JEL | JEL | JEL | JEL | |
|---|---|---|---|---|---|---|---|
| Date | 12/28 | 12/28 | 1/5 | 1/5 | 1/5 | 1/5 | |
| Time | 09:00 | 13:00 | 08:35 | 08:35 | 24:00 | 24:00 | hrs. |
| Light | yes | yes | no | yes | no | yes | |
| Photofrin | 0 | 2.5 | 0 | 0 | 2.5 | 2.5 | ug/mL. |
| Sodium | 152.0 | 138.1 | 145.0 | 159.5 | 156.8 | 158.3 | mM. |
| Potassium | 4.07 | 7.36 | 18.62 | 3.69 | 6.25 | 3.54 | mM |
| Calcium | .06 | 0.05 | 0.06 | 0.06 | 0.07 | 0.07 | mM |
| Glucose | 153 | 89 | 72 | 88 | 79 | 83 | mg/dL. |
|  | 158 | 92 | 71 | 87 | 79 | 83 | mg/dL |
| Osmotic Frag. | | | | | | | |
| Begin: | 0.46 | 0.46 | 0.46 | 0.46 | 0.46 | 0.46 | % |
| 50%: | 0.40 | 0.40 | 0.44 | 0.44 | 0.44 | 0.44 | % |
| complete: | 0.34 | 0.30 | 0.34 | 0.34 | 0.34 | 0.34 | % |
| Sugar Wat.lys | 0.100 | 0.260 | 0.645 | 0.000 | 1.095 | .009 | O.D.540 |
| Fibrinogen: | 327 | 227 | 325 | 325 | 341 | 298 | mg/dl |
| PT: | QNS | 13.9 | 11.3 | 11.6 | 12.0 | 13.1 | secs |
| APTT | 35.5 | 37.0 | 27.8 | 26.2 | 29.4 | 29.3 | secs. |
| Factor Def. Scn. | | | | | | | |
| Factor II | neg. | neg. | neg. | neg. | neg. | neg. | |
| Factor V | neg | neg | neg. | neg. | neg. | neg. | |
| Factor VII | neg | neg | neg | neg. | neg. | neg. | |
| factor X | neg | neg | neg. | neg. | neg. | neg. | |
| Factor VIII | neg. | neg. | neg. | neg. | neg. | neg. | |
| IX | neg | neg | neg. | neg. | neg. | neg. | |
| XI | neg | neg | neg. | neg. | neg. | neg. | |
| XII | neg | neg | neg. | neg. | neg. | neg. | |
| CBC | | | | | | | |
| WBC | 6.5 | 6.4 | 7.0 | 8.1 | 3.3 | 3.8 | Thous. |
| RBC | 4.53 | 4.51 | 4.45 | 2.37 | 4.83 | 4.77 | Mill. |
| HGB | 15.1 | 14.9 | 13.1 | 7.35 | 14.5 | 14.1 | g/dL. |
| HCT | 43.2 | 45.2 | 47.4 | 21.6 | 43.9 | 42.4 | % |
| MCV | 102 | 100.3 | 107.0 | 88.0 | 91.0 | 91.0 | fl. |
| MCH | 33.3 | 33.1 | 29.5 | 30.4 | 30.0 | 29.8 | pg. |
| MCHC | 32.7 | 33.0 | 27.6 | 34.1 | 32.9 | 33.5 | g/dL. |
| RDW | 13.4 | 12.5 | 23.0 | 9.8 | 14.1 | 11.8 | % |
| Platelets | 145 | 151 | 127.0 | 235 | 85 | 88 | thous. |
| Differential | | | | | | | |
| Total polys | 70 | 57 | 69 | 61 | 66 | 70 | % |
| segs | 68 | 57 | 69 | 61 | 65 | 70 | % |
| bands | 2 | 0 | 0 | 0 | 1 | 0 | % |
| lymphs. | 25 | 38 | 25 | 29 | 30 | 26 | % |
| monos. | 4 | 4 | 5 | 7 | 3 | 1 | % |
| eosin. | 1 | 1 | 1 | 3 | 0 | 1 | % |
| baso | 0 | 0 | 0 | 0 | 1 | 0 | % |
| Direct Coombs | neg. | +/− IGg + | neg. | neg. | neg. | neg. | |
| Serum Elec | NA | NA | | | | | |
| Albumin | NA | NA | 16.72 | 54.83 | 39.18 | 52.99 | % |
| alpha 1-Glob | NA | NA | 3.01 | 5.68 | 4.99 | 5.60 | % |
| alpha 2-Glob | NA | NA | 5.17 | 10.55 | 7.88 | 10.72 | % |
| beta - Glob | NA | NA | 62.39 | 12.00 | 31.92 | 13.43 | % |
| gamma- Glob | NA | NA | 12.71 | 16.95 | 16.02 | 17.26 | % |
| 02 Dissociatn | | | | | | | |

TABLE II-continued

| RESULTS: Human Blood From Normal, Healthy Volunterrs | | | | | | |
|---|---|---|---|---|---|---|
| p50 | | 29 | | 29 | 29 | mmHg |
| Comments | | *1 | *2 | *1 | | |

*1 Sample hemolysed due to age of cuvet.
*2 CBC reflects inadequate loading of unopet since if the RBC had been low due to hemolysis the MCH would have risen to reflect the hemolysis.

| Donor | LH | LH | LH | LH | RB | RB | |
|---|---|---|---|---|---|---|---|
| Date | 1/6/87 | 1/6/87 | 1/6/87 | 1/6/87 | 1/7/87 | 1/7/87 | |
| Time | 0847 | 0847 | 1130 | 1130 | 0850 | 0850 | hrs. |
| Light | no | yes | no | yes | no | yes | |
| Photofrin | 0 | 0 | 2.5 | 2.5 | 0 | 0 | ug/mL. |
| Soldium | 157.5 | 158.4 | 155.7 | 155.3 | 155.5 | 154.5 | mM |
| Potassium | 3.37 | 3.26 | 3.34 | 3.37 | 3.44 | 3.37 | mM |
| Calcium | 0.06 | 0.06 | 0.06 | 0.06 | 0.06 | 0.06 | mM |
| Glucose | 66 | 64 | 65 | 61 | 81 | 80 | mg/dL |
|  | 65 | 63 | 65 | 62 | 81 | 77 | mg/dL |
| Osmotic Frag. | | | | | | | |
| Begin: | 0.50 | 0.05 | 0.50 | 0.50 | 0.46 | 0.46 | % |
| 50%: | 0.46 | 0.46 | 0.46 | 0.46 | 0.44 | 0.44 | % |
| complete: | 0.34 | 0.34 | 0.30 | 0.30 | 0.30 | 0.30 | % |
| Sugar Wat.lys | | | change in OD @ 540 nm: | | | | |
|  | 0.003 | 0.019 | 0.000 | 0.000 | 0.000 | 0.000 | |
| Fibrinogen: | 377 | 320 | 358 | 302 | 286 | 298 | mg/dL. |
| PT: | 10.9 | QNS | 11.5 | 12.5 | 11.9 | 11.9 | secs. |
| APTT | 24.0 | 25.0 | 25.0 | 27.0 | 34.7 | 36.5 | secs. |
| Factor Def. Scn. | | | | | | | |
| Factor II | neg. | neg. | neg. | neg. | neg. | neg. | |
| Factor V | neg. | neg. | neg. | neg. | neg. | neg. | |
| Factor VII | neg. | neg. | neg. | neg. | neg. | neg. | |
| Factor X | neg. | neg. | neg. | neg. | neg. | neg. | |
| Factor VIII | neg. | neg. | neg. | neg. | neg. | neg. | |
| IX | neg. | neg. | neg. | neg. | neg. | neg. | |
| XI | neg. | neg. | neg. | neg. | neg. | neg. | |
| XII | neg. | neg. | neg. | neg. | neg. | neg. | |
| CBC | | | | | | | |
| WBC | 8.6 | 6.8 | 5.1 | 6.1 | 3.2 | 3.3 | thous |
| RBC | 4.12 | 3.78 | 5.22 | 5.99 | 5.22 | 5.59 | millns. |
| HGB | 12.7 | 11.6 | 16.4 | 18.3 | 15.2 | 16.4 | g/dL. |
| HCT | 38.2 | 34.8 | 48.1 | 55.2 | 45.9 | 48.9 | % |
| MCV | 92.7 | 92.1 | 92.3 | 92.0 | 87.8 | 87.4 | fl. |
| MCH | 30.8 | 30.7 | 31.5 | 30.6 | 29.1 | 29.3 | pg. |
| MCHC | 33.2 | 33.4 | 34.1 | 33.2 | 33.1 | 33.6 | g/dL |
| RDW | 12.0 | 11.1 | 12.8 | 12.5 | 14.5 | 14.8 | % |
| Platelets | 248 | 225 | 134 | 88 | 153 | 155 | thous. |
| Differential | | | | | | | |
| Total polys | 60 | 64 | 66 | 76 | 64 | 66 | % |
| segs | 60 | 64 | 66 | 74 | 64 | 66 | % |
| bnads | 0 | 0 | 0 | 2 | 0 | 0 | % |
| lymphs | 29 | 30 | 2 | 7 | 21 | 26 | % |
| monos | 8 | 3 | 18 | 8 | 14 | 7 | % |
| eos | 3 | 1 | 11 | 7 | 21 | 26 | % |
| baso | 0 | 2 | 3 | 2 | 0 | 0 | % |
| Direct Coombs | neg. | neg. | neg. | neg. | neg | neg. | % |
| Serum Elect | | | | | | | |
| Albumin: | 62.80 | 64.16 | 62.11 | 64.52 | 57.05 | 56.27 | % |
| alpha 1-Glob | 3.27 | 3.58 | 3.61 | 3.42 | 3.63 | 3.41 | % |
| alpha 2-Glob | 10.24 | 9.73 | 11.59 | 10.86 | 8.15 | 8.33 | % |
| beta - Glob: | 13.25 | 11.45 | 11.89 | 11.20 | 14.08 | 13.48 | % |
| gamma - Glob | 10.44 | 11.07 | 10.80 | 10.00 | 17.87 | 17.73 | % |

| Donor | RB | RB | | | | |
|---|---|---|---|---|---|---|
| Date | 1/7/8 | 1/7/87 | | | | |
| Time | 1140 | 1140 | hrs. | | | |
| Light | no | yes | | | | |
| Photofrin | 2.5 | 2.5 | ug/mL. | | | |
| Sodium | 157.4 | 157.4 | mM | | | |
| Potassium | 3.74 | 3.92 | mM | | | |
| Calcium | 0.06 | 0.07 | mM | | | |
| Glucose | 65 | 65 | mg/dL | | | |
|  | 63 | 62 | mg/dL | | | |
| Osmotic Frag. | | | | | | |
| Begin: | 0.46 | 0.46 | % | | | |
| 50%: | 0.43 | 0.42 | % | | | |
| complete: | 0.34 | 0.34 | % | | | |
|  | Sugar Wat.lys | | 0.000 | 0.006 | change in OD @ 540 nm: | |
|  | Fibrinogen: | | 298 | 237 | mg/dL. | |
|  | PT: | | 13.1 | 13.6 | secs. | |
|  | APTT | | 33.7 | 39.7 | secs. | |
|  | Factor Def. Scn. | | | | | |
|  | Factor II | | neg. | neg. | | |

TABLE II-continued

| RESULTS: Human Blood From Normal, Healthy Volunterrs | | | |
|---|---|---|---|
| Factor V | neg. | neg. | |
| Factor VII | neg. | neg. | |
| Factor X | neg. | neg. | |
| Factor VIII | neg. | neg. | |
| IX | neg. | neg. | |
| XI | neg. | neg. | |
| XII | neg. | neg. | |
| CBC | | | |
| WBC | 3.0 | 3.2 | thous |
| RBC | 5.55 | 5.69 | millns |
| HGB | 16.3 | 16.9 | g/dL |
| HCT | 48.3 | 50.0 | % |
| MCV | 87.0 | 87.8 | fl. |
| MCH | 29.3 | 29.7 | pg. |
| MCHC | 33.6 | 33.7 | g/dL |
| RDW | 15.4 | 16.0 | % |
| Platelets | 150 | 139 | thous |
| Differential | | | |
| Total polys | 55 | 48 | % |
| segs | 55 | 58 | % |
| bands | 0 | 0 | % |
| lymphs | 26 | 24 | % |
| monos | 14 | 16 | % |
| eos | 3 | 2 | % |
| baso | 2 | 0 | % |
| Direct Coombs | neg. | polysp & IgGl+ wk C3dneg. | |
| Serum Elect.: | | | |
| Albumin | 56.52 | 56.15 | % |
| alpha 1-Glob | 3.66 | 3.43 | % |
| alpha 2-Glob | 8.12 | 8.23 | % |
| beta - Glob | 13.59 | 13.46 | % |
| gamma -Glob | 18.10 | 18.74 | % |

Survival Studies: Blood smears prepared and examined for proteinacious debris: no unusual debris noted.

TABLE III

| RESULTS: Human Blood Spiked With Herpes Simplex Virus Type I | | | |
|---|---|---|---|
| Donor | HS | HS | |
| Date | 1/12/87 | 1/12/87 | |
| Time | 0830 | 0830 | hrs. |
| Light | no | yes | |
| Photofrin | 0 | 2.5 | ug/mL. |
| Sodium | 159.2 | 159.8 | mM |
| Potassium | 4.15 | 3.97 | mM |
| Calcium | 0.07 | 0.07 | mM |
| Glucose | 56 | 61 | mg/dL |
|  | 56 | 62 | mg/dL |
| Osmotic Frag. | | | |
| Begin: | 0.46 | 0.46 | % |
| 50%: | 0.44 | 0.44 | % |
| complete: | 0.36 | 0.34 | % |
| Sugar Wat.lys | 0 | 0 | OD @ 540 nm |
| Fibrinogen: | 336 | 377 | mg/dL. |
| PT: | 13.3 | 11.4 | secs. |
| APTT | 39.3 | 31.5 | secs. |
| Factor Def. Scn. | | | |
| Factor II | neg. | neg. | |
| Factor V | neg. | neg. | |
| Factor VII | neg. | neg. | |
| Factor X | neg. | neg. | |
| Factor VIII | neg. | neg. | |
| IX | neg. | neg. | |
| XI | neg. | neg. | |
| XII | neg. | neg. | |
| CBC... | | | |
| WBC | 7.8 | 8.6 | thous |
| RBC | 5.09 | 5.25 | millns. |
| HGB | 15.9 | 16.3 | g/dL. |
| HCT | 47.3 | 48.8 | % |
| MCV | 92.6 | 92.7 | fl. |
| MCH | 31.3 | 31.0 | pg. |
| MCHC | 33.8 | 33.3 | g/dL. |
| RDW | 10.2 | 10.5 | % |
| Platelets | 221 | 193 | thous. |
| Differential | | | |
| Total polys | 78 | 78 | % |
| segs | 78 | 77 | % |
| bands | 0 | 1 | % |
| lymphs | 14 | 7 | % |
| monos | 6 | 11 | % |
| eos | 2 | 4 | % |
| baso | 0 | 0 | % |
| Direct Coombs | neg. | neg. | |
| Serum Elect: | | | |
| Albumin: | 62.52 | 64.68 | % |
| alpha 1-Glob | 2.85 | 2.81 | % |
| alpha 2-Glob | 10.32 | 10.54 | % |
| beta - Glob | 13.36 | 12.63 | % |
| gamma -Glob | 10.95 | 9.33 | % |
| Comments | | | |

TABLE IV

RESULTS: Human Blood From Patients With AIDS

| Donor | BL | BL | BD | BD | |
|---|---|---|---|---|---|
| Date | 2/11/87 | 2/11/87 | 4/14/87 | 4/14/87 | |
| Time | 0925 | 0925 | 0900 | 0900 | hrs. |
| Light | no | yes | no | yes | |
| Photofrin | 0 | 2.5 | 0 | 2.5 | ug/ml. |
| Sodium | 152 | 155 | 160.7 | 163.0 | mM |
| Potassium | 3.8 | 3.8 | 3.32 | 3.43 | mM |
| Calcium | 0.10 | 0.007 | 0.06 | 0.06 | mM |
| Glucose | 75 | 75 | 66 | 67 | mg/dl |
| | | | 66 | 67 | mg/dl |
| Osmotic Frag. | | | | | |
| Begin: | 44 | 44 | 46 | 44 | % |
| 50%: | 44 | 42 | 41 | 41 | % |
| complete: | 34 | 34 | 34 | 34 | % |
| Sugar Wat.lys | 0.017 | 0.030 | 0.000 | 0.000 | OD @ 540 nm |
| Fibrinogen: | 378 | 315 | 227 | 183 | mg/dl. |
| PT: | 11.6 | 13.0 | 13.0 | 14.5 | secs. |
| APTT | 29.5 | 35.4 | 47.9 | 50.1 | secs. |
| Factor Def. Scn. | | | | | |
| Factor II | neg. | neg. | neg | neg | |
| Factor V | neg. | neg. | neg | neg | |
| Factor VII | neg. | neg. | neg | neg | |
| Factor X | neg. | neg. | neg | neg | |
| Factor VIII | neg. | neg. | neg. | neg. | |
| IX | neg. | neg. | neg. | neg. | |
| XI | neg. | neg. | neg. | neg. | |
| XII | neg. | neg. | neg. | neg. | |
| CBC | | | | | |
| WBC | 2.5 | 2.2 | 2.3 | 2.3 | thsnds. |
| RBC | 2.91 | 2.45 | 5.33 | 5.86 | millns. |
| HGB | 9.0 | 7.7 | 15.6 | 16.8 | g/dL. |
| HCT | 27.1 | 22.9 | 47.3 | 52.4 | % |
| MCV | 92.9 | 93.3 | 88.7 | 89.3 | fl. |
| MCH | 30.8 | 31.5 | 29.2 | 28.7 | pg. |
| MCHC | 33.5 | 33.7 | 33.0 | 32.1 | g/dL. |
| RDW | 9.2 | 9.1 | 11.6 | 11.9 | % |
| Platelets | 120 | 122 | 47 | 45 | thsnds. |
| Differential | | | | | |
| Total polys | 43 | 30 | 25 | 28 | % |
| segs | 35 | 54 | 20 | 21 | % |
| bands | 8 | 12 | 5 | 7 | % |
| lymphs | 39 | 54 | 36 | 31 | % |
| monos | 16 | 12 | 9 | 9 | % |
| eos | 2 | 4 | 30 | 30 | % |
| baso | | | | 2 | % |
| Direct Coombs | neg(poly specific | 1+wk polysp. 1+wk IgG C3 neg. sal.con −neg. | neg | +/− 1+IgG C3 neg. | |
| Serum Electro | | | | | |
| Albumin | 46.34 | 42.93 | 48.77 | 52.61 | % |
| alpha1-Glob. | 3.17 | 2.73 | 3.07 | 3.14 | % |
| alpha2-Glob. | 12.42 | 12.01 | 9.10 | 7.51 | % |
| beta-glob. | 14.22 | 21.46 | 13.90 | 13.16 | % |
| gamma-glob. | 23.84 | 20.86 | 25.16 | 23.58 | % |
| O2 dissoc. | NR | NR | 28 | 25 | mm Hg at p50 |
| Comments | Hemolysis of sample(LIPPBL) noted after approx. 2.5 ml. had been run through flow cell. Noted apparent high sed-rate of patient. | | | | |

The abbreviations used in Tables II to IV are as follows:

| ABBREVIATION | FULL NAME |
|---|---|
| Photofrin | Photofrin II ™, from Johnson and Johnson, containing approximately 90% of dihematoporphyrin ether, DHE |
| Osmotic Frag | Osmotic Fragility |
| Sugar Wat. lys. | Sugar Water Lysis tests |
| PT | Prothrombin Time |
| APTT | Activated Partial Thromboplastin Time |
| Factor Def. Scn. | Factor Deficiency Screen |
| CBC | Complete Blood Count |
| WBC | White Blood Cell |
| RBC | Red Blood Cell |
| HGB | Hemoglobin |
| HCT | Hematocrit |
| MCV | Mean Corpuscular Volume |
| MCH | Mean Corpuscular Hemoglobin Concentration |
| Total polys | Total polymorphonucleocytes |
| segs | segmented neutrophils |
| lymphs. | lymphocytes |
| monos. | monocytes |
| eosin | eosinophils |
| baso | basophils |

-continued

| ABBREVIATION | FULL NAME |
|---|---|
| Serum Elec | Serum Electrophoresis |
| Glob | Globulin |
| IgG | Immunoglobulin G |
| C3 | Complement fragment 3 |
| O2 dissoc. | Oxygen dissociaton |
| sal. con | Saline concentration |
| neg. | Negative |
| NR | No result |
| sed-rate | sedimentation-rate |

The following abbreviated units are also used in Tables II to IV.

| ABBREVIATED UNITS | FULL NAME |
|---|---|
| hrs | hours |
| ug/ml | microgram per milliliter |
| mM | microgram per milliliter |
| mg/dl | milligram per deciliter |
| O.D. 540 | Optical Density at 540 nanometer |
| secs | seconds |
| Thous. | Thousand per microliter |
| Mill. | Millions per microliter |
| g/dL | gram per deciliter |
| fl. | femtoliter |
| pg | picogram |
| p | partial pressure |

It can be seen from these Tables that photo-irradiation in the presence of Photofrin II TM did not have a deleterious effect on blood. It is important in evaluating the data to appreciate the scaling down of normal laboratory procedures that occurred in these examples. The flow rate attained during these experiment was about 23 microliters per minute. Handling small aliquots on blood in a darkened room and avoiding them drying out presented logistical problems. In some control samples appreciable hemolysis occured, this was found to arise from kinking of the cuvet tubing following repeated use in the high intensity light. This kinking caused pressure to build up in the sample, resulting in lysis. Whenever this problem arose the cuvet causing the problem was discarded. Viability of the irradiated samples containing Photofrin II TM was based on the following parameters: Potassium and glucose were well within the limits established for blood banked whole blood; RDW which is the standard deviation of red cell size was unchanged or lower centration (MCH) showed no elevation; osmotic fragility was unaffected; sugar water lysis tests showed no lysis following irradiation, but the same results are usually found in banked blood and is therefore not a contraindication for transfusing the blood. Serum electrophoresis could only be quantified as a percentage and not in absolute terms.

In two of the samples from patients with AIDS, prolongation of the APTT test occurred. One patient, however, had already had a prolonged APTT. In both these patients, the factor deficient screen test indicate that this prolongation did not arise from selective destruction of any of the coagulation factors but might have arisen from changes in the optical qualities of the plasma which could affect the optical clot detection devices.

In summary, photoirradiation of human blood outside the human body in the presence of a photoactive compound such as Photofrin IITM did not affect the viability of the human blood as determined by currently accepted blood bank criteria.

Effect of Photofrin II TM and Light on Human Whole Blood Containing Herpes simplex Virus Type 1

*Herpes simplex* virus type 1 (HSV-1), the MacIntyre strain, was purchased from the American Type Culture Collection (ATCC) and propagated in Vero cells (ATCC) to a concentration of $10^6$-$10^7$ plaque forming units (PFU) per milliliter (ml). This solution was used as stock virus. Twenty milliliters of blood were collected from a healthy volunteer in acid citrate dextrose and the blood was divided into 0.9 ml aliquots. A volume of 0.1 ml of stock virus was added to eight separate aliquots of blood.

Photofrin II TM (From Johnson and Johnson. A photoactive dye that contains approximately 90% of pure dihematoporphyrin ether (DHE)), was added to duplicate tubes of the virus-blood mixture and a set of tubes containing blood only. The concentrations of Photofrin II TM employed were 2.5, 10 and 20µg/ml. Samples representing each concentration of Photofrin II TM in the blood virus mixture were irradiated while moving through the flow cell by light at a wave length of approximately 635 nm with an energy density of about 5 J/cm$^2$. Approximately 30–60 min elapsed between the addition of each concentration of Photofrin II TM and exposure of light in the flow cell. During the holding period, the samples were maintained at 4° C. Except during the time of irradiation, all manipulations were carried out with minimal exposure to extraneous light. During a 15–30 minute period of time, approximately 0.7 ml of the irradiated sample was collected. A sample of virus mixed with blood but not containing Photofrin II TM was also irradiated under the same conditions. During the holding period and the period of irradiation the duplicate samples of virus and blood containing different concentrations of Photofrin II TM were held in the dark. In addition, samples of human blood (without virus) containing different concentrations of Photofrin II TM and a sample of blood spiked with virus only were also maintained in the dark.

Each sample including the stock virus were assayed on vero cells for PFU/ml of HSV-I. The assay consisted of growing vero cells in minimal essential medium with Hanks balanced salt solution supplemented with 10% fetal bovine serum, L-glutamine and antibiotics. Hepes buffer (2%) was added for growth in open plates (twelve well microplates from Costar). Ten fold dilutions of each sample were prepared and 0.1 ml of the appropriate dilution for each individual sample was adsorbed at 37° C. for 1.5 hr on a cell monolayer from which the growth medium had been removed. After the adsorption period, the cell monolayer was washed and an overlay consisting of equal volumes of 2X strength L-15 medium and 2% methylcellulose was added. Following an appropriate incubation time at 37° C. (about 4 days), the overlay medium was removed. Monolayers were fixed with methanol and stained with giemsa to elaborate the presence of plaques. The plaques were counted using a dissecting microscope at a magnification of 20X.

TABLE V

| PHOTOINACTIVATION OF BLOOD SPIKED WITH HERPES SIMPLEX TYPE-1 (HSV-1) CARRIED OUT IN A FLOW CELL SYSTEM | | | |
|---|---|---|---|
| Concentration of PII/ml | PFU/ml in Dark | PFU/ml in Light | % Reduction In PFU-Light to Dark |
| 2.5 µg | $1 \times 10^4$ | $1.2 \times 10^1$ | 99.88 |

TABLE V-continued

PHOTOINACTIVATION OF BLOOD SPIKED WITH
HERPES SIMPLEX TYPE-1 (HSV-1)
CARRIED OUT IN A FLOW CELL SYSTEM

| Concentration of PII/ml | PFU/ml in Dark | PFU/ml in Light | % Reduction In PFU-Light to Dark |
|---|---|---|---|
| 10 μg | $9 \times 10^3$ | $1.25 \times 10^1$ | 99.86 |
| 20 μg | $9 \times 10^3$ | $0.5 \times 10^1$ | 99.94 |

PFU: Plaque forming unit
PII: Photofrin II TM
HSV-1: Diluted 1:10 in blood and irradiated yielded $1 \times 10^4$ PFU/ml. Virus diluted in blood and not irradiated yielded $5 \times 10^4$ PFU/ml.

The results of the experiment can be observed in Table V. It is clear that Photofrin II TM in a concentration as low as 2.5 μg/ml, in combination with light at a wavelength of 625–635 nm having an energy density of 5 J/cm², achieved a near total (larger than 99.88%) kill of HSV-1 in human whole blood. The use of larger amounts of Photofrin II TM resulted in a similar reduction in viral infectivity. Blood samples containing the three different concentrations of Photofrin II TM showed no evidence of cellular toxicity when assayed in the vero cells as described above.

Effect of Photofrin II TM and Light on Human Immunodeficiency Virus (HIV)

The human immunodeficiency virus (HIV) has also been irradiated in the flow cell. Approximately $4 \times 10^4$ infectious units (IU)/ml of cell-free HIV was prepared in tissue culture. The stock virus was then diluted 1:2 in tissue culture medium and six 1 ml aliquots of HIV were prepared. Irradiation studies were carried out in a similar manner as described above for the photoinactivation of HSV-1 in blood. All samples were, however, maintained at room temperature throughout the experiment. One of the above aliquots of HIV was passed through the flow cell in the dark. A second aliquot of HIV was irradiated in the flow cell at 5 J/cm² for approximately 30 minutes which yielded approximately 0.7 ml of irradited fluid. Three other samples, each containing different concentrations of Photofrin II TM, namely, 2.5, 10 and 20 μg/ml, were irradiated. All six samples were then placed in cell culture at five different dilutions: Neat (no dilution) $10^{-1}$, $10^{-2}$, $10^{-3}$, and $10^{-4}$. Supernatants from each culture were collected at prescribed intervals and assayed for HIV activity by the reverse transcriptase assay, according to the procedure reported by Chanh, et al. (Eur. Mol. Biol. Organization J., 5: 3065–3071, 1986)

It can be seen from Table VI that an appropriate amount of Photofrin II TM in combination with light at a wavelength of 625–635 nm having an energy density of 5J/cm² achieved a near complete kill of human immunodeficiency virus (HIV), the culprit for AIDS, in the flow cell.

TABLE VI

PHOTOINACTIVATION OF A CULTURE OF HUMAN
IMMUNODEFICIENCY VIRUS IN A FLOW CELL SYSTEM[a]

| Concentration of PII/ml | Infectious Units Per Milliliter[b] | | % Kill In Light |
|---|---|---|---|
| | In Dark | In Light (5J/cm²) | |
| 0 | $2 \times 10^4$ | $2 \times 10^4$ | 0 |
| 2.5 μg | — | C | C |
| 10 μg | — | $1^d$ | 100 |
| 20 μg | — | $1^d$ | 100 |

PII: Photofrin II TM
[a]The infectious units of the human immunodeficiency virus were unaffected whether or not the culture of virus was channelled through the flow cell system.
[b]As determined by reversed transcriptase activity.
C Percent kill could not be determined.
[d]No detectable activity of the enzyme reverse transcriptase.

These studies suggest that the major target for photodynamic damage of Photofrin II TM in viruses is envelope related.

The method of the present invention provides an effective and efficient means for eradicating infectious pathogenic contaminants from body fluids outside the body of an animal or a human.

Unlike the metabolic clearance of a photoactive drug in normal tissues observed in a live animal or human as described in the U.S. Pat. No. 4,649,151 to Dougherty et. al., animal or blood outside the body is not subject to this physiological or metabolic action by various body organs. Consequently, there is no mechanism for detoxification or "cleaning" of the human whole blood outside a body.

Surprisingly, despite the absence of the physiological or metabolic "cleansing" mechanism, human whole blood outside the human body shows a remarkable tolerance towards a photoactive compound such as Photofrin II TM. By all accounts, the human whole blood remains unchanged in the presece of certain concentrations of this photoactive compound. Equally surprising, external irradiation of normal human whole blood containing a photoactive compound with a specified wavelength of absorption causes no detectable damage to the whole blood when used at selected concentrations and intensity. Although outside the human body, after such treatment, the human whole blood is still unchanged by all currently acceptable standards. Although the infectious biological contaminants, such as parasites, bacteria or viruses encapsulated by a protein envelope, are totally different from human malignant tumor cells, a photoactive compound such as Photofrin II TM has been found to have a selective affinity toward these infectious pathogenic contaminants contained in human whole blood outside the human body. Moreover, such a compound can be photoactivated outside the human body to cause the demise of these infectious biological pathogenic contaminants to which the compound has preferentially attached.

It is clear that the present invention is well adapted to carry out the objects and attain the ends and advantages mentioned herein as well as those inherent in the invention. While presently preferred embodiments of the invention have been described for purposes of this disclosure, numerous changes may be made which will readily suggest themselves to those skilled in the art and which are accomplished within the spirit of the invention disclosed and as defined in the appended claims.

What is claimed is:

1. A method for eradicating infectious pathogenic biological contaminants from body fluids outside the body prior to introduction of the decontaminated body fluids into the body of a patient, said method comprising:

admixing an effective, non-toxic amount of a photoactive compound with the body fluid to produce a resulting body fluid, the photoactive compound having an affinity to be selectively bound to the contaminants;

passing the resulting fluid under flow conditions through a cell assembly having a predetermined flow path; and irradiating the resulting fluid in the cell assembly as same passes through the flow path with an effective level of radiation in the region of the visible spectrum, with a wavelength range upwards of about 400 nm to about 1000 nm, for an effective period of time such that the radiation penetrates the resulting fluid and exposes the photoactive-compound-bound contaminants to the radiation so as to eradicate such contaminants while maintaining the viability of said body fluids to produce viable decontaminated body fluids.

2. The eradicating method as recited in claim 1 further comprising the step of selecting a body fluid from the group consisting of whole blood, blood plasma, serum, and fluids from plasmapheresis.

3. The eradicating method as recited in claim 1 further comprising the step of selecting a body fluid comprising semen.

4. The eradicating method as recited in claim 1 further comprising the step of selecting a photoactive compound comprising a mixture of porphrins, at least a portion of the molecules of said porphrin mixture having the molecular formula:

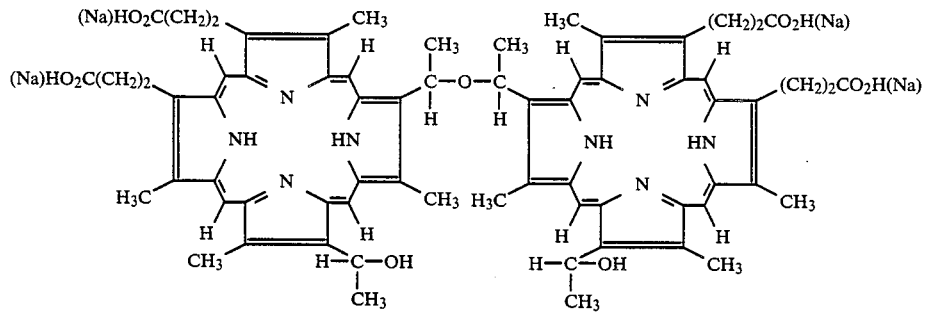

said molecules with said formula being fluorescent, photosensitizing, having the capability of selectively binding to said pathogenic biological contaminants, forming a high molecular weight aggregate with absorption peaks in the ultraviolet and visible spectra in water at approximately 365, 505, 537, 575, and 615 nanometers, absorption peaks in the infrared spectrum at approximately 3.0, 3.4, 7.1, 8.1, 9.4, 12 and 15 microns, absorption peaks in carbon-13 nuclear magnetic resonance study at approximately 9.0, 18.9, 24.7, 34.5, 62, 94.5, 130-145, 171.7 ppm and possible 118 and 127 relative to a 37.5 ppm resonance peak of dimethyl sulfoxide and additional absorption peaks in carbon-13 nuclear magnetic resonance study at approximately 27.9 ppm and 68.4 ppm relative to the resonance peak of tetramethylsilane in deuterated chloroform solvent; and at least 50 percent of the porphyrins in said mixture being of said molecule having said molecular formula.

5. The method of claim 4 wherein the amount of said mixture of porphyrins admixed with said fluids is from about 0.1 to about 50 micrograms per milliliter of body fluid.

6. The method of claim 5 wherein the amount of said mixture of porphyrins admixed with said fluids is from about 2 to 50 micrograms per milliliter of body fluid.

7. The method of claim 1 wherein the level of radiation is produced by a light source having a wavelength of from about 400 to about 1000 nm and an energy density of from about 0.1 to about 50 $J/cm^2$.

8. The method of claim 7 wherein the level of radiation is produced by a light source having a wavelength of from about 600 to about 700 nm and an energy density from about 1 to about 20 $J/cm^2$.

9. The eradicating method as recited in claim 1 further comprising the step of selecting body fluids which contain pathogenic biological contaminants comprising an envelope-containing virus.

10. The eradicating method as recited in claim 9 further comprising the step of selecting the envelope-containing virus from the group consisting of Herpesviridae, Poxviridae, Iridoviridae, Hepadnaviridae, orthomyxoviridae, and Paramyxoviridae.

11. The eradicating method as recited in claim 9 further comprising the step of selecting the envelope-containing virus from the group consisting of Rhabdoviridae, Bunyaviridae, Filoviridae, Nodaviridae, and Togaviridae.

12. The eradicating method as recited in claim 9 further comprising the step of selecting the envelope-containing virus from the group consisting of Flaviviridae, Retroviridae, and Arenaviridae.

13. The eradicating method as recited in claim 12 further comprising the step of selecting the Retrovirividae comprising a human immunodeficiency virus.

14. The eradicating method as recited in claim 1 further comprising the step of selecting body fluids which contain pathogenic biological contaminants comprising a bacteria selected from the group consisting of *Streptococcus faecalis* and *Bacillus subtilis*.

15. The eradicating method as recited in claim 1 further comprising the step of selecting body fluids which contain pathogenic biological contaminants comprising a malarial parasite.

16. The eradicating method as recited in claim 1 further comprising the step of selecting body fluids which contain pathogenic biological contaminants comprising a trypanosomal parasite.

17. A method for externally purifying blood products to eradicate pathogenic biological contaminants selected from the group consisting of envelope-containing viruses, bacteria, malarial, and trypanosomal parasites prior to introduction of the decontaminated blood products intravenously into a patient, said method comprising:

admixing an effective amount of a photoactive compound with the blood products to bind the contaminant with the photoactive compound, said photoactive compound comprising a mixture of porphyrins, at least a portion of the molecules of said porphyrin mixture having the molecular formula:

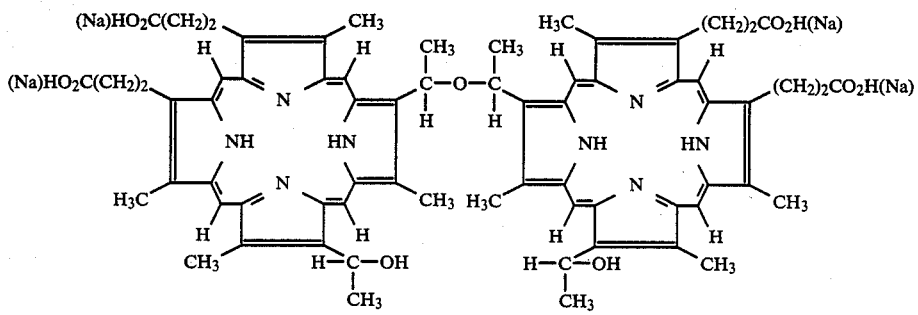

said molecules with said formula being fluorescent, phtosensitizing, having the capability of selectively binding to said pathogenic biological contaminants, forming a high molecular weight aggregate with absorption peaks in the ultraviolet and visible spectra in water at approximately 365, 505, 537, 575, and 615 nanometers, absorption peaks in the infrared spectrum at approximately 3.0, 3.4, 6.4, 7.1, 8.1, 9.4, 12 and 15 microns, absorption peaks in carbon-13 nuclear magnetic resonance study at approximately 9.0, 18.9, 24.7, 34.5, 62, 94.5, 130-145, 171.7 ppm and possible 118 and 127 relative to a 37.5 ppm resonance peak of dimethyl sulfoxide and additional absorption peaks in carbon-13 nuclear magnetic resonance study at approximately 27.9 ppm and 68.4 ppm relative to the resonance peak of tetramethylsilane in deuterated chloroform solvent; and at least 50 percent of the porphyrins in said mixture being of said molecule having said molecular formula;

passing the blood products containing the porphyrins-bound contaminants through a cell assembly having a flow path exposable to a radiation source capable of irradiating the blood products as same travels along the flow path; and irradiating the blood products with a radiation source in the region of visible spectrum, with a wavelength upwards of about 400 nm to about 1000 nm for an effective period of time to permit the radiation to penetrate through the blood products in the flow path of the cell assembly and eradicate the contaminants while maintaining the viability of components in said blood products.

18. The method of claim 17 wherein the amount of said mixture of porphyrins admixed with said blood products is from about 0.1 to about 50 micrograms per milliliter of blood products.

19. The method of claim 18 wherein the amount of said mixture of porphyrins admixed with said blood products is from about 2 to about 50 micrograms per milliliter of blood products.

20. The method of claim 17 wherein the level of radiation is produced by a light source having a wavelength of from about 400 to about 700 nm and an energy density of from about 0.1 to about 50 J/cm$^2$.

21. The method of claim 20 wherein the level of radiation is produced by a light source having a wavelength of from about 600 to about 700 nm and an energy density of from about 1 to about 20 J/cm$^2$.

22. The eradication method as recited in claim 17 further comprising the step of selecting blood products which contain pathogenic biological contaminants comprising an envelope-containing virus.

23. The eradicating method as recited in claim 22 further comprising the step of selecting the envelope-containing virus from the group consisting of Herpesviridae, Poxviridae, Iridoviridae, Hepadnaviridae, Orthomyxoviridae, and Paramyxoviridae.

24. The eradicating method as recited in claim 22 further comprising the step of selecting the envelope-containing virus from the group consisting of Rhabdoviridae, Bunyaviridae, Filoviridae, Nodaviridae, and Togaviridae.

25. The eradication method as recited in claim 22 further comprising the step of selecting the envelope-containing virus from the group consisting of Flaviviridae, Retroviridae, and Arenaviridae.

26. The eradicating method as recited in claim 25 further comprising the step of selecting the Retroviridae comprising a human immunodeficiency virus.

27. The eradicating method as recited in claim 17 further ℗r comprising the step of selecting blood products which contain pathogenic biological contaminants comprising a bacteria selected from the group consisting of *Streptococcus faecalis* and *Bacillus subtilis*.

28. The eradicating method as recited in claim 17 further comprising the step of selecting body fluids which contain pathogenic biological contaminants comprising a malarial parasite.

29. The eradicating method as recited in claim 17 further comprising the step of selecting blood products which contain pathogenic biological contaminants comprising a trypanosomal parasite.

30. A method for eradicating infectious pathogenic biological contaminants from body tissues outside the body prior to transplanting the decontaminated body tissues onto the body of the patient, said method comprising:

removing by excision from a donor a piece of human tissue that is translucent to light;

admixing a effective, non-toxic amount of a photoactive compound with the body tissue suspended in a physiologically acceptable saline solution, the photoactive compound having an affinity to be selectively bound to the contaminants; and irradiating the resulting suspension of the body tissue gently a(g)gitated in a physiologically acceptable saline solution with an effective level of radiation in the region of the visible spectrum, with a wavelength range upwards of about 400 nm to about 1000 nm, for an effective period of time such that the radiation penetrates the body tissue and exposes the photoactive-compound-bound contaminants to the radiation so as to eradicate such contaminants while maintaining the viability of said body tissue to produce viable decontaminated body tissues suitable for transplantation.

31. The eradicating method as recited in claim 30 further comprising the step of selecting a body tissue from the group consisting of skin and cornea.

32. The eradicating method as recited in claim 30 further comprising the step of selecting a photoactive compound comprising a mixture of porphyrins, at least a portion of the molecules of said porphyrin mixture having the molecular formula:

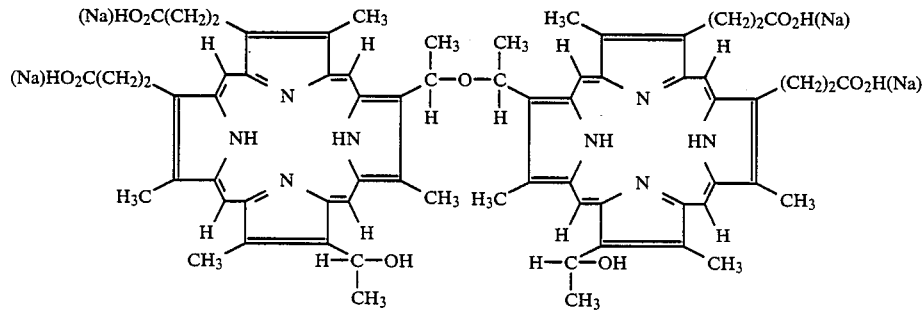

said molecules with said formula being fluorescent, photosensitizing, having the capability of selectively binding to said pathogenic biological contaminants, forming a high molecular weight aggregate with absorption peaks in the ultraviolet and visible spectra in water at approximately 365, 505, 537, 575, and 615 nanometers, absorption peaks in the infrared spectrum at approximately 3.0, 3.4, 6.4, 7.1, 8.1, 9.4, 12 and 15 microns, absorption peaks in carbon-13 nuclear magnetic resonance study at approximately 9.0, 18.9, 24.7, 34.5, 62, 94.5, 130-145, 171.7 ppm and possible 118 and 127 relative to a 37.5 ppm resonance peak of dimethyl sulfoxide and additional absorption peaks in carbon-13 nuclear magnetic resonance study at approximately 27.9 ppm and 68.4 ppm relative to the resonance peak of tetramethylsilane in deuterated chloroform solvent; and at least 50 percent of the porphyrins in said mixture being of said molecule having said molecular formula.

33. The method of claim 30 wherein the level of radiation is produced by a light source having a wavelength of from about 400 to about 700 nm and an energy density of from about 0.1 to about 20 J/cm$^2$.

34. The method of claim 33 wherein the level of radiation is produced by a light source having a wavelength of from about 600 to about 700 nm and an energy density from about 1 to about 20 J/cm$^2$.

35. The eradicating method as recited in claim 30 further comprising the step of selecting body tissues which contain pathogenic biological contaminants comprising an envelope-containing virus.

36. The eradicating method as recited in claim 35 further comprising the step of selecting the envelope-containing virus from the group consisting of Herpesviridae, Poxviridae, Iridoviridae, Hepadnaviridae, Orthomyxoviridae, and Paramyxoviridae.

37. The eradicating method as recited in claim 35 further comprising the step of selecting the envelope-containing virus from the group consisting of Rhabdoviridae, Bunyaviridae, Filoviridae, Nodaviridae, and Togaviridae.

38. The eradicating method as recited in claim 35 further comprising the step of selecting the envelope-containing virus from the group consisting of Flaviviridae, Retroviridae, and Arenaviridae.

39. The eradicating method as recited in claim 38 further comprising the step of selecting the Retroviridae comprising a human immunodeficiency virus.

40. The eradicating method as recited in claim 30 further comprising the step of selecting body tissues which contain pathogenic biological contaminants comprising a bacteria selected from the group consisting of *Streptococcus faecalis* and *Bacillus subtilis*.

41. The eradicating method as recited in claim 30 further comprising the step of selecting body tissues which contain pathogenic biological contaminants comprising a malarial parasite.

42. The eradicating method as recited in claim 30 further comprising the step of selecting body tissues which contain pathogenic biological contaminants comprising a trypanosomal parasite.

43. A method for extracorporeal treatment of the blood of a patient infected with infectious pathogenic biological contaminants said method comprising:

removing blood from the body of a patient infected with infectious pathogenic biological contaminants;

adding to said blood, before the removal of the blood, an effective, non-toxic amount of photoactive compound having an affinity to be selectively bound to the infectious contaminants;

passing said treated blood through a cell assembly having a predetermined flow path;

irradiating said contaminated blood admixed with photoactive compound in the cell assembly as same passes through the flow path with an effective level of radiation in the region of visible spectrum, with a wavelength range upwards of about 400 nm to about 1000 nm, for an effective period of time such that the radiation penetrates the blood and exposes the photoactive-compound-bound infectious contaminants to the radiation so as to eradicate such infectious contaminants while maintaining the viability of components in said blood to produce a viable and decontaminated blood; and
returning said viable and decontaminated blood to the patient's body.

44. The eradicating method as recited in claim 43 further comprising the step of selecting a photoactive compound comprising a mixture of porphyrins, at least a portion of the molecules of said porphyrin mixture having the molecular formula:

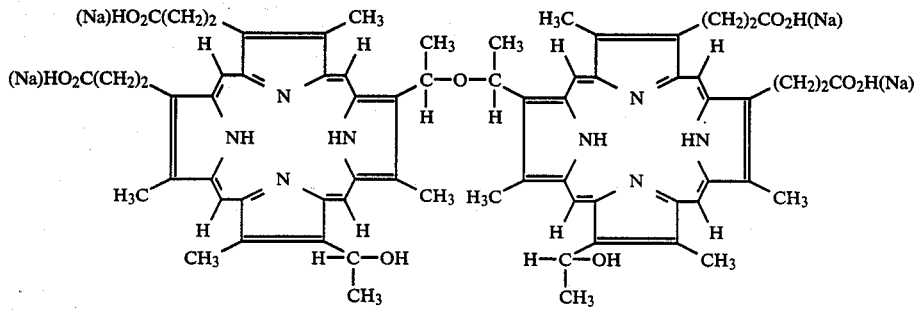

said molecules with said formula being fluorescent, photosensitizing, having the capability of selectively binding to said pathogenicbiological contaminants, forming a high molecular weight aggregate with absorption peaks in the ultraviolet and visible spectra in water at approximately 365, 505, 537, 575, and 615 nanometers, absorption peaks in the infrared spectrum at approximately 3.0, 3.4, 6.4, 7.1, 8.1, 9.4, 12 and 15 microns, absorption peaks in carbon-13 nuclear magnetic resonance study at approximately 9.0, 18.9, 24.7, 34.5, 62, 94.5, 130-145, 171.7 ppm and possible 118 and 127 relative to a 37.5 ppm resonance peak of dimethyl sulfoxide and additional absorption peaks in carbon-13 nuclear magnetic resonance study at approximately 27.9 ppm and 68.4 ppm relative to the resonance peak of tetramethylsilane in deuterated chloroform solvent; and at least 50 percent of the porphyrins in said mixture being of said molecule having said molecular formula.

45. The eradicating method as recited in claim 44 further comprising the step of administering said mixture of porphyrins to the patient prior to the removal of the blood from the patient's body for irradiation.

46. The eradicating method as recited in claim 45 further comprising the step of administering said mixture of porphyrins to the patient between about one hour and about one week prior to the removal of the patient's blood for irradiation.

47. The eradicating method as recited in claim 45 further comprising the step of administering said mixture of porphyrins at a dosage from about 0.5 mg to about 40 mg per kg of body weight of the patient.

48. The eradicating method as recited in claim 44 further comprising the step of admixing said mixture of porphyrins, dissolved in a physiologically acceptable saline solution, with the blood after said blood has been removed from the patient's body.

49. The eradicating method as recited in claim 48 further comprising the step of admixing said mixture of porphyrins with said blood in an amount from about 0.1 to about 50 micrograms per milliliter of said blood.

50. The eradicating method as recited in claim 49 further comprising the step of admixing said mixture of porphyrins with said blood in an amount from about 2 to about 50 micrograms per milliliter of said blood.

51. The method of claim 43 wherein the level of radiation is produced by a light source having a wavelength of from about 600 to about 1000 nm and an energy density of from about 1 to about 50 J/cm$^2$.

52. The method of claim 51 wherein the level of radiation is produced by a light source having a wavelength of from about 600 to about 700 nm and an energy density of from about 1 to about 20 J/cm$^2$.

53. The eradicating method as recited in claim 43 further comprising the step of selecting a blood which contains pathogenic biological contaminants comprising an envelope-containing virus.

54. The eradicating method as recited in claim 53 further comprising the step of selecting the envelope-containing virus from the group consisting of Herpesviridae, Poxviridae, Iridoviridae, Hepadnaviriae, Orthomyxoviridae, and Paramyxoviridae.

55. The eradicating method as recited in claim 53 further comprising the step of selecting the envelope-containing virus from the group consisting of Rhabdoviridae, Bunyaviridae, Filoviridae, Nodaviridae, and Togaviridae.

56. The eradicating method as recited in claim 53 further comprising the step of selecting the envelope-containing virus from the group consisting of Flaviviridae, Retroviridae, and Arenaviridae.

57. The eradicating method as recited in claim 56 further comprising the step of selecting the Retroviridae comprising a human immunodeficiency virus.

58. The eradicating method as recited in claim 43 further comprising the step of selecting a blood which contains pathogenic biological contaminants comprising a bacteria selected from the group consisting of *Streptococcus faecalis* and *Bacillus subtilis*.

59. The eradicating method as recited in claim 43 further comprising the step of selecting the pathogenic biological contaminants comprising a malarial parasite.

60. The eradicating method as recited in claim 43 further comprising the step of selecting a blood which contains pathogenic biological contaminants comprising a trypanosomal parasite.

61. A method for extracorporeal treatment of the blood of a patient infected with infectious pathogenic biological contaminants said method comprising:
removing blood from the body of a patient infected with infectious pathogenic foreign biological contaminants;
adding to said blood, after the removal of the blood, an effective, non-toxic amount of photoactive compound having an affinity to be selectively bound to the infectious contaminants;

passing said treated blood through a cell assembly having a pedetermined flow path;

irradiating said contaminated blood admixed with photoactive compound in the cell assembly as the same passes through the flow path with an effective level of radiation in the region of visible spectrum, with a wavelength range upwards of about 400 nm to about 1000 nm, for an effective period of time such that the radiation penetrates the blood and exposes the photoactive-compound-bound infectious contaminants to the radiation so as to eradicate such infectious contaminants while maintaining the viability of compounds in said blood to produce a viable and decontaminated blood; and returning said viable and decontaminated blood to the patient's body.

62. The eradicating method as recited in claim 32 and further comprising the step of admixing said mixture of porphyrins, from about 0.1 to about 50 micrograms per milligram of body tissue, in a physiologically acceptable saline solution with said suspension of body tissue.

63. The eradicating method as recited in claim 62 and further comprising the step of admixing said mixture of porphyrins, from about 2 to 50 micrograms per milligram of body tissue, in a physiologically acceptable saline solution with said suspension of body tissue.

* * * * *